US008277444B2

(12) United States Patent
Arnold et al.

(10) Patent No.: US 8,277,444 B2
(45) Date of Patent: Oct. 2, 2012

(54) TREATMENT OF ATRIAL FIBRILLATION BY OVERLAPPING CURVILINEAR LESIONS

(75) Inventors: Jeffrey M. Arnold, Wellesley, MA (US); Edward L. Sinofsky, Dennis, MA (US); Lincoln S. Baxter, Centerville, MA (US); Norman E. Farr, Monument Beach, MA (US)

(73) Assignee: CardioFocus, Inc., Marlborough, MA (US)

( * ) Notice: Subject to any disclaimer, the term of this patent is extended or adjusted under 35 U.S.C. 154(b) by 6 days.

(21) Appl. No.: 11/504,354

(22) Filed: Aug. 15, 2006

(65) Prior Publication Data

US 2007/0078451 A1    Apr. 5, 2007

Related U.S. Application Data

(63) Continuation of application No. 10/357,156, filed on Feb. 3, 2003, now Pat. No. 8,025,661, which is a continuation-in-part of application No. 09/924,394, filed on Aug. 7, 2001, now Pat. No. 6,579,285, which is a continuation-in-part of application No. 09/390,964, filed on Sep. 7, 1999, now Pat. No. 6,270,492, which is a continuation-in-part of application No. 08/991,130, filed on Dec. 16, 1997, now Pat. No. 5,947,959, which is a continuation-in-part of application No. 08/827,631, filed on Apr. 10, 1997, now Pat. No. 5,908,415, which is a continuation of application No. 08/303,605, filed on Sep. 9, 1994, now abandoned.

(51) Int. Cl.
*A61B 18/18* (2006.01)

(52) U.S. Cl. .................. 606/41; 606/2; 606/19; 606/42; 606/52; 607/88; 607/101; 128/898

(58) Field of Classification Search ................ 606/2–16, 606/32, 41; 607/88–94; 128/898
See application file for complete search history.

(56) References Cited

U.S. PATENT DOCUMENTS 3,417,745 A    12/1968    Sheldon
3,821,510 A    6/1974    Muncheryan
(Continued)

FOREIGN PATENT DOCUMENTS
DE    94117543    11/1994
(Continued)

OTHER PUBLICATIONS

Bredikis, J. et al. "Laser Destruction of the Atrioventricular Bundle Using the Cardiac Endoscope" Kardlologiia, 1988, 28(8): 94-96.
(Continued)

*Primary Examiner* — Aaron Roane
(74) *Attorney, Agent, or Firm* — Leason Ellis LLP

(57) ABSTRACT

Ablation methods and instruments are disclosed for creating lesions in tissue, especially cardiac tissue for treatment of arrhythmias and the like. Percutaneous ablation instruments in the form of coaxial catheter bodies are disclosed having at least one central lumen therein and having one or more balloon structures at the distal end region of the instrument. The instruments include an energy emitting element which is independently positionable within the lumen of the instrument and adapted to project radiant energy through a transmissive region of a projection balloon to a target tissue site to form a series of lesions on the target tissue.

12 Claims, 14 Drawing Sheets

U.S. PATENT DOCUMENTS

| | | |
|---|---|---|
| 4,224,929 A | 9/1980 | Furihata et al. |
| 4,233,493 A | 11/1980 | Nath et al. |
| 4,336,809 A | 6/1982 | Clark |
| 4,445,892 A | 5/1984 | Hussein et al. |
| 4,585,298 A | 4/1986 | Mori et al. |
| 4,625,724 A | 12/1986 | Suzuki et al. |
| 4,660,925 A | 4/1987 | McCaughan, Jr. |
| 4,701,166 A | 10/1987 | Groshong et al. |
| 4,718,417 A | 1/1988 | Kittrell et al. |
| 4,819,632 A | 4/1989 | Davies et al. |
| 4,852,567 A | 8/1989 | Sinofsky |
| 4,860,743 A | 8/1989 | Abela |
| 4,862,886 A | 9/1989 | Clarke et al. |
| 4,878,492 A | 11/1989 | Sinofsky et al. |
| 4,878,725 A | 11/1989 | Hessel et al. |
| 4,913,142 A | 4/1990 | Kittrell et al. |
| 4,961,738 A | 10/1990 | Mackin |
| 5,026,367 A | 6/1991 | Leckrone et al. |
| 5,030,201 A | 7/1991 | Palestrant |
| 5,053,033 A | 10/1991 | Clarke |
| 5,071,417 A | 12/1991 | Sinofsky |
| 5,078,681 A | 1/1992 | Kawashima |
| 5,090,959 A | 2/1992 | Samson et al. |
| 5,109,859 A | 5/1992 | Jenkins |
| 5,125,925 A | 6/1992 | Lundahl |
| 5,133,709 A | 7/1992 | Prince |
| 5,140,987 A | 8/1992 | Schuger et al. |
| 5,151,096 A | 9/1992 | Khoury |
| 5,151,097 A | 9/1992 | Daikuzono et al. |
| 5,163,935 A | 11/1992 | Black et al. |
| 5,169,395 A | 12/1992 | Narciso, Jr. |
| 5,188,632 A | 2/1993 | Goldenberg |
| 5,188,634 A | 2/1993 | Hussein et al. |
| 5,190,538 A | 3/1993 | Hussein et al. |
| 5,196,005 A | 3/1993 | Doiron et al. |
| 5,207,699 A | 5/1993 | Coe |
| 5,209,748 A | 5/1993 | Daikuzono et al. |
| 5,219,346 A | 6/1993 | Wagnieres et al. |
| 5,242,438 A | 9/1993 | Saadatmanesh et al. |
| 5,261,904 A | 11/1993 | Baker et al. |
| 5,269,777 A | 12/1993 | Doiron et al. |
| RE34,544 E | 2/1994 | Spears |
| 5,330,465 A | 7/1994 | Doiron et al. |
| 5,337,381 A | 8/1994 | Biswas et al. |
| 5,350,375 A | 9/1994 | Deckelbaum et al. |
| 5,363,458 A | 11/1994 | Pan et al. |
| 5,368,564 A | 11/1994 | Savage |
| 5,380,316 A | 1/1995 | Aita et al. |
| 5,395,362 A | 3/1995 | Sacharoff et al. |
| 5,401,270 A | 3/1995 | Muller et al. |
| 5,409,483 A | 4/1995 | Campbell et al. |
| 5,417,653 A | 5/1995 | Sahota et al. |
| 5,423,805 A | 6/1995 | Brucker et al. |
| 5,427,119 A | 6/1995 | Swartz et al. |
| 5,431,647 A | 7/1995 | Purcell, Jr. et al. |
| 5,437,660 A | 8/1995 | Johnson et al. |
| 5,441,497 A | 8/1995 | Narciso, Jr. |
| 5,464,404 A | 11/1995 | Abela et al. |
| 5,482,037 A | 1/1996 | Borghi et al. |
| 5,497,774 A | 3/1996 | Swartz et al. |
| 5,507,725 A | 4/1996 | Savage et al. |
| 5,531,664 A * | 7/1996 | Adachi et al. ............ 600/149 |
| 5,536,265 A | 7/1996 | van den Bergh et al. |
| 5,575,766 A | 11/1996 | Swartz et al. |
| 5,613,965 A | 3/1997 | Muller |
| 5,643,253 A | 7/1997 | Baxter et al. |
| 5,649,923 A | 7/1997 | Gregory et al. |
| 5,680,860 A | 10/1997 | Imran |
| 5,690,611 A | 11/1997 | Swartz et al. |
| 5,702,438 A | 12/1997 | Avitall |
| 5,722,401 A | 3/1998 | Pietroski et al. |
| 5,725,522 A | 3/1998 | Sinofsky |
| 5,759,619 A | 6/1998 | Jin et al. |
| 5,769,843 A | 6/1998 | Abela et al. |
| 5,772,590 A | 6/1998 | Webster, Jr. |
| 5,773,835 A | 6/1998 | Sinofsky |
| 5,779,646 A | 7/1998 | Koblish et al. |
| 5,782,239 A | 7/1998 | Webster, Jr. |
| 5,782,899 A | 7/1998 | Imran |
| 5,800,482 A | 9/1998 | Pomeranz et al. |
| 5,807,395 A | 9/1998 | Mulier et al. |
| 5,823,955 A | 10/1998 | Kuck et al. |
| 5,824,005 A | 10/1998 | Motamedi et al. |
| 5,830,209 A | 11/1998 | Savage et al. |
| 5,833,682 A | 11/1998 | Amplatz et al. |
| 5,843,073 A | 12/1998 | Sinofsky |
| 5,845,646 A | 12/1998 | Lemelson |
| 5,860,974 A | 1/1999 | Abele |
| 5,885,278 A | 3/1999 | Fleischman |
| 5,891,133 A | 4/1999 | Murphy-Chutorian |
| 5,891,134 A | 4/1999 | Goble et al. |
| 5,904,651 A | 5/1999 | Swanson et al. |
| 5,908,415 A | 6/1999 | Sinofsky |
| 5,931,834 A | 8/1999 | Murphy-Chutorian et al. |
| 5,938,660 A | 8/1999 | Swartz et al. |
| 5,947,959 A | 9/1999 | Sinofsky |
| 5,971,983 A | 10/1999 | Lesh |
| 5,995,875 A | 11/1999 | Blewett et al. |
| 6,004,269 A | 12/1999 | Crowley et al. |
| 6,012,457 A | 1/2000 | Lesh |
| 6,024,740 A | 2/2000 | Lesh et al. |
| 6,064,902 A | 5/2000 | Haissaguerre et al. |
| 6,071,279 A | 6/2000 | Whayne et al. |
| 6,071,281 A | 6/2000 | Burnside et al. |
| 6,071,282 A | 6/2000 | Fleischman |
| 6,071,302 A | 6/2000 | Sinofsky et al. |
| 6,086,581 A | 7/2000 | Reynolds et al. |
| 6,090,084 A | 7/2000 | Hassett et al. |
| 6,102,905 A | 8/2000 | Baxter et al. |
| 6,117,101 A | 9/2000 | Diederich et al. |
| 6,120,496 A | 9/2000 | Whayne et al. |
| 6,146,379 A | 11/2000 | Fleischman et al. |
| 6,159,203 A | 12/2000 | Sinofsky |
| 6,161,543 A | 12/2000 | Cox et al. |
| 6,164,283 A | 12/2000 | Lesh |
| 6,179,835 B1 | 1/2001 | Panescu et al. |
| 6,214,002 B1 | 4/2001 | Fleischman et al. |
| 6,217,510 B1 | 4/2001 | Ozawa et al. |
| 6,235,025 B1 | 5/2001 | Swartz et al. |
| 6,237,605 B1 | 5/2001 | Vaska et al. |
| 6,245,064 B1 | 6/2001 | Lesh et al. |
| 6,251,109 B1 | 6/2001 | Hassett et al. |
| 6,254,599 B1 | 7/2001 | Lesh et al. |
| 6,270,492 B1 | 8/2001 | Sinofsky |
| 6,305,378 B1 | 10/2001 | Lesh |
| 6,312,427 B1 | 11/2001 | Berube et al. |
| 6,314,962 B1 | 11/2001 | Vaska et al. |
| 6,325,797 B1 | 12/2001 | Stewart et al. |
| 6,383,151 B1 | 5/2002 | Diederich et al. |
| 6,394,949 B1 | 5/2002 | Crowley et al. |
| 6,416,511 B1 | 7/2002 | Lesh et al. |
| 6,423,055 B1 | 7/2002 | Farr et al. |
| 6,423,058 B1 | 7/2002 | Edwards et al. |
| 6,471,697 B1 | 10/2002 | Lesh |
| 6,485,485 B1 | 11/2002 | Winston et al. |
| 6,500,174 B1 | 12/2002 | Maguire et al. |
| 6,502,576 B1 | 1/2003 | Lesh |
| 6,503,247 B2 | 1/2003 | Swartz et al. |
| 6,514,249 B1 | 2/2003 | Maguire et al. |
| 6,544,262 B2 | 4/2003 | Fleischman |
| 6,547,780 B1 | 4/2003 | Sinofsky |
| 6,572,609 B1 | 6/2003 | Farr et al. |
| 6,579,285 B2 | 6/2003 | Sinofsky |
| 6,605,084 B2 | 8/2003 | Acker et al. |
| 6,626,900 B1 | 9/2003 | Sinofsky et al. |
| 6,635,054 B2 | 10/2003 | Fjield et al. |
| 6,669,655 B1 | 12/2003 | Acker et al. |
| 6,896,673 B2 * | 5/2005 | Hooven ............ 606/32 |
| 6,932,809 B2 | 8/2005 | Sinofsky |
| 6,942,657 B2 | 9/2005 | Sinofsky et al. |
| 7,207,984 B2 | 4/2007 | Farr et al. |
| 7,935,108 B2 | 5/2011 | Baxter et al. |
| 8,025,661 B2 | 9/2011 | Arnold et al. |
| 2001/0030107 A1 | 10/2001 | Simpson |
| 2002/0019627 A1 | 2/2002 | Maguire et al. |
| 2002/0029062 A1 | 3/2002 | Satake |
| 2002/0065512 A1 | 5/2002 | Fjield et al. |

| | | | |
|---|---|---|---|
| 2002/0091383 A1 | 7/2002 | Hooven | |
| 2002/0107511 A1 | 8/2002 | Collins et al. | |
| 2002/0115995 A1 | 8/2002 | Lesh et al. | |
| 2002/0120264 A1 | 8/2002 | Crowley et al. | |
| 2002/0183739 A1 | 12/2002 | Long | |
| 2003/0050632 A1 | 3/2003 | Fjield et al. | |
| 2003/0065307 A1 | 4/2003 | Lesh | |
| 2003/0069620 A1 | 4/2003 | Li | |
| 2003/0111085 A1 | 6/2003 | Lesh | |
| 2003/0120270 A1 | 6/2003 | Acker | |
| 2003/0171746 A1 | 9/2003 | Fleischman | |
| 2004/0006333 A1 | 1/2004 | Arnold et al. | |
| 2004/0054360 A1 | 3/2004 | Schwartz et al. | |
| 2004/0122290 A1 | 6/2004 | Irion et al. | |
| 2005/0038419 A9 | 2/2005 | Arnold et al. | |
| 2005/0065504 A1 | 3/2005 | Melsky et al. | |
| 2005/0222558 A1 | 10/2005 | Baxter et al. | |
| 2005/0234436 A1 | 10/2005 | Baxter et al. | |
| 2005/0288654 A1 | 12/2005 | Nieman et al. | |
| 2006/0253113 A1 | 11/2006 | Arnold et al. | |
| 2007/0078451 A1 | 4/2007 | Arnold et al. | |
| 2008/0039746 A1 | 2/2008 | Hissong et al. | |
| 2008/0108870 A1 | 5/2008 | Wiita et al. | |
| 2008/0195088 A1 | 8/2008 | Farr et al. | |
| 2009/0221996 A1 | 9/2009 | Lesh et al. | |
| 2009/0221997 A1 | 9/2009 | Arnold et al. | |
| 2009/0275934 A1 | 11/2009 | Baxter et al. | |
| 2009/0299354 A1 | 12/2009 | Melsky et al. | |
| 2009/0326320 A1 | 12/2009 | Sinofsky et al. | |
| 2011/0082449 A1 | 4/2011 | Melsky et al. | |
| 2011/0082450 A1 | 4/2011 | Melsky et al. | |
| 2011/0082451 A1 | 4/2011 | Melsky | |
| 2011/0082452 A1 | 4/2011 | Melsky et al. | |
| 2011/0245822 A1 | 10/2011 | Baxter et al. | |
| 2011/0245828 A1 | 10/2011 | Baxter et al. | |

FOREIGN PATENT DOCUMENTS

| | | |
|---|---|---|
| EP | 0214712 | 3/1987 |
| EP | 0292621 | 11/1988 |
| EP | 0292695 | 11/1988 |
| EP | 0299448 | 1/1989 |
| EP | 0311458 | 4/1989 |
| EP | 0437181 | 7/1991 |
| EP | 0437183 | 7/1991 |
| EP | 0439629 | 8/1991 |
| EP | 0598984 | 8/1994 |
| EP | 0792664 | 9/1997 |
| EP | 1072231 | 1/2001 |
| FR | 2798371 A | 3/2001 |
| JP | 2003-210028 A | 7/2003 |
| JP | 2004-065076 A | 3/2004 |
| WO | WO 9217243 | 10/1992 |
| WO | WO 9306888 | 4/1993 |
| WO | WO 9319680 | 10/1993 |
| WO | WO 9325155 | 12/1993 |
| WO | WO 9417434 | 8/1994 |
| WO | WO 9426184 | 11/1994 |
| WO | WO 9607451 | 3/1996 |
| WO | WO 9737714 | 10/1997 |
| WO | WO 00/67656 | 11/2000 |
| WO | WO 00/67832 | 11/2000 |
| WO | WO 01/03599 | 1/2001 |
| WO | WO 0113812 | 3/2001 |
| WO | WO 01/64123 | 9/2001 |
| WO | WO 02/096479 | 12/2002 |
| WO | WO 2004-110258 | 12/2004 |

OTHER PUBLICATIONS

Chevalier, P. et al. "Thoracoscopic Epicardial Radiofrequency Ablation for Vagal Atrial Fibrillation in Dogs" Pace, 1999, 22: 880-886.

Froelich, J. et al. "Evaluation of a Prototype Steerable Angioscopic Laser Catheter in a Canine Model: A Feasibility Study" Cardiovasc Intervent Radiol, 1993 16: 235-238.

Fujimura, O. at al. "Direct In Vivo Visualization of Right Cardiac Anatomy by Fiberoptic Endoscopy" Angiology; 1995, 46 (3): 201-208.

Fujimura, O. et al. "Direct In Vivo Visualization of Right Cardiac Anatomy by Fiberoptic Endoscopy: Observation of Radiofrequency-Induced Acute Lesions Around the Ostium of the Coronary Sinus" European Heart J., 1994, 15: 534-540.

Gamble, W. and Innis, R. "Experimental Intracardiac Visualization" NEJM 1967, 276(25): 1397-1403.

Hirao, K. et al. "Transcatheter Neodymlum-Yttrium-Aluminum-Garnet Laser Coagulation of Canine Ventricle Using a Balloon-Tipped Cardioscope" Jpn Circ J., 1997, 81: 695-703.

Keane, D. et al. "Pulmonary Vein Isolation for Atrial Fibrillation" Rev Cardiovasc Med., 2002, 3(4): 167-175.

Kuo, C. et al. "In Vivo Angloscoplc Visualization of Right Heart Structure in Dogs by Means of a Balloon-Tipped Fiberoptic Endoscope: Potential Role in Percutaneous Ablative Procedures." American Heart J., 1994, 127: 187-197.

Nakagawa, H. et al. "Cardioscopic Catheter Ablation with Non-contact, Pulsed Nd:YAG Laser Using Saline Inflated Balloon Catheter," Presentation JACC 1998; 31: 118A-119A.

Obelienius, V. et al. "Transvenous Ablation of the Atrioventricular Conduction System by Laser Irradiation Under Endoscopic Control" Lasers in Surgery Medicine, 1985, 5: 469-474.

Roggan, A., et al. "Optical Properties of Circulating Human Blood in the Wavelength Range 400-2400 nm" J Biomedical Optics, 1999,4(1): 36-46.

Saliba, W. et al. "Circumferential Ultrasound Ablation for Pulmonary Vein Isolation: Analysis of Acute and Chronic Failures" J Cardiovascular Electrophysiology, 2002, 13(10): 957-961.

Shure, D. et al. "Identification of Pulmonary Emboli in the Dog: Comparison of Angioscopy and Perfusion Scanning" Circulation, 1981, 64(3): 618-621.

Shure, D., et al. "Fiberoptic Angioscopy: Role in the Diagnosis of Chronic Pulmonary Arterial Obstruction" Ann Int Med., 1985, 103: 844-850.

Tanabe, T. et al. "Cardiovascular Fiberoptic Endoscopy: Development and Clinical Application" Surgery, 1980, 87(4): 375-379.

Uchida, Y. et al. "Fiberoptic Angioscopy of Cardiac Chambers, Valves, and Great Vessels Using a Guiding Balloon Catheter in Dogs." American Heart J., 1998, 115(6): 1297-1302.

Uchida, Y. et al. "Percutaneous Pulmonary Angioscopy Using a Guiding Balloon Catheter" Clin. Cardiol., 1988, 11: 143-148.

Vanermen, H. et al. "Minimally Invasive Video-Assisted Mitral Valve Surgery: From Port-Access Towards a Totally Endoscopic Procedure" J Card Surg., 2000, 15: 51-60.

Yamamoto, N et al. "Nonfluoroscopic Guidance for Catheter Placement Into the Coronary Sinus under Direct Vision Using a Balloon-Tipped Cardioscope" PACE, 1998; 21: 1724-1729.

* cited by examiner

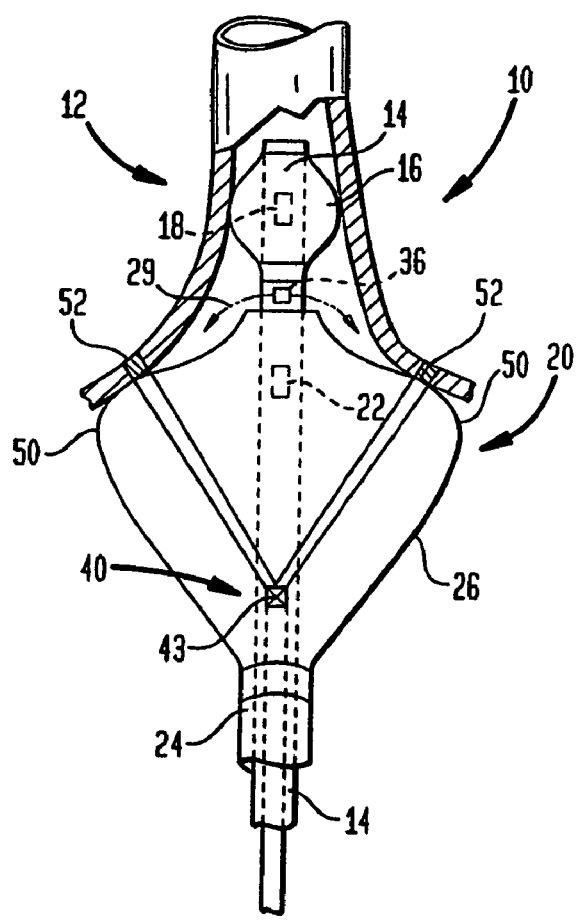
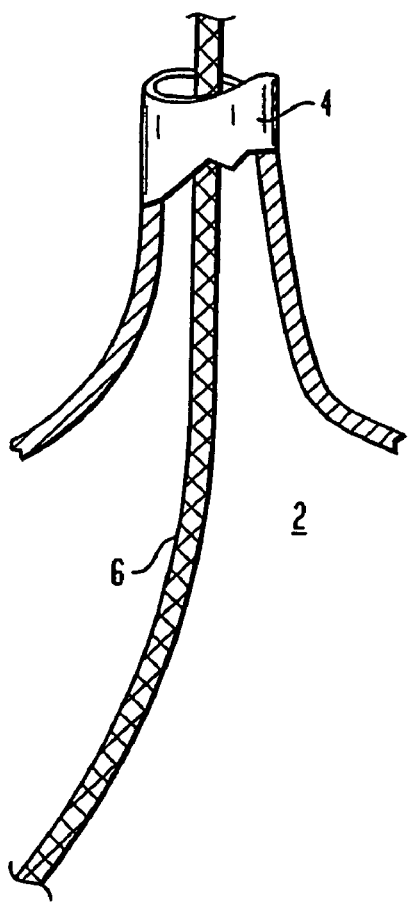

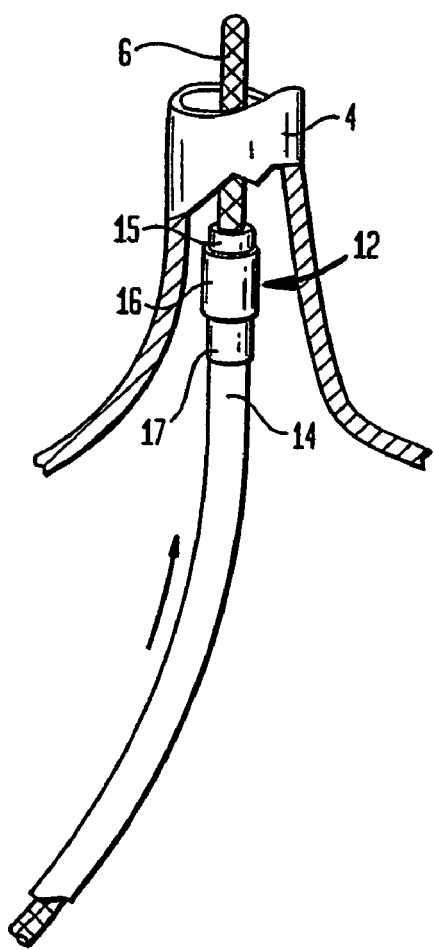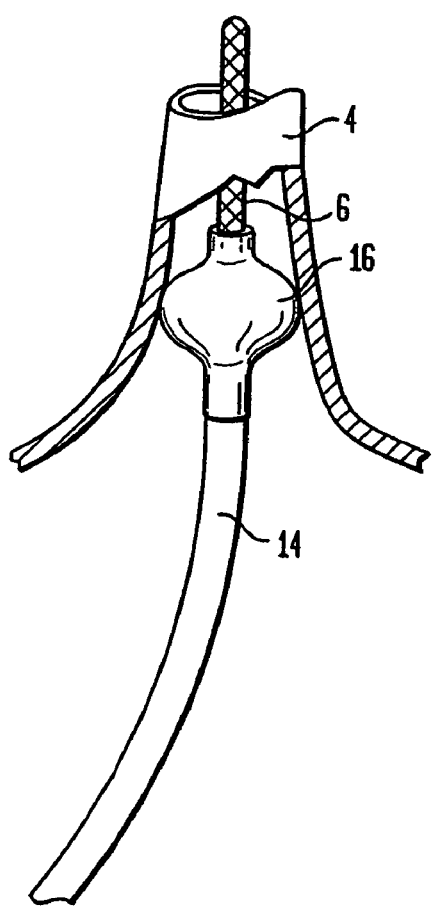

FIG. 9
FIG. 10
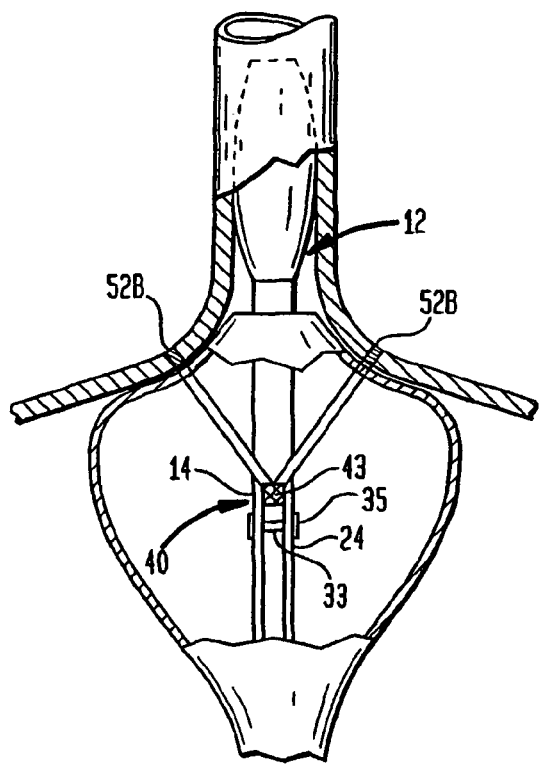
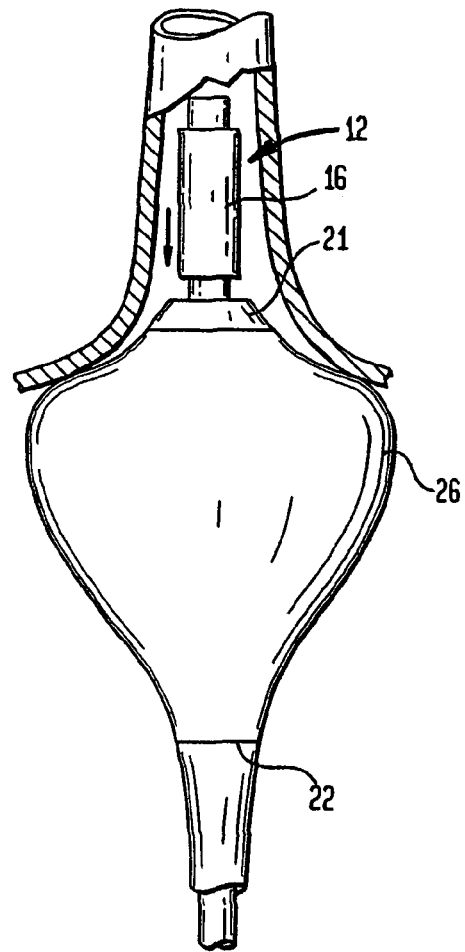

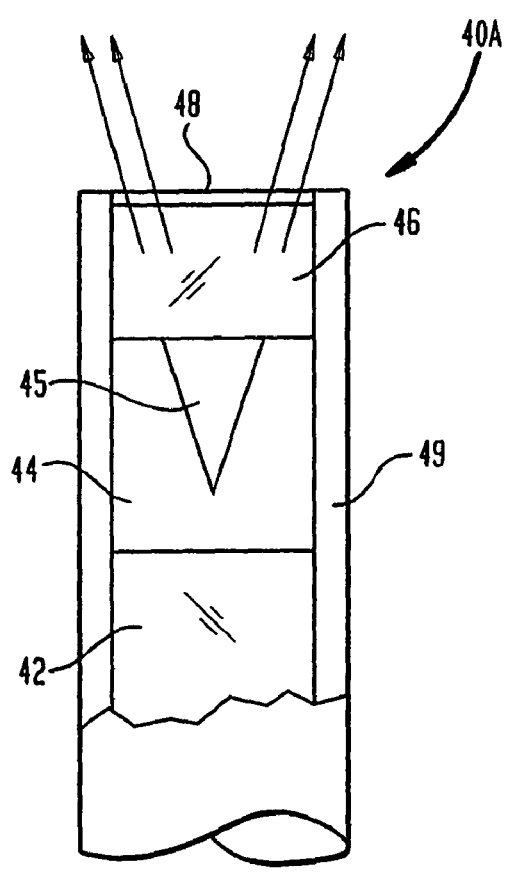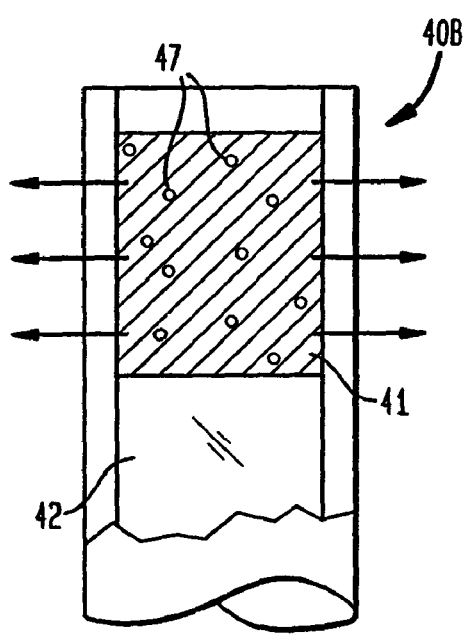

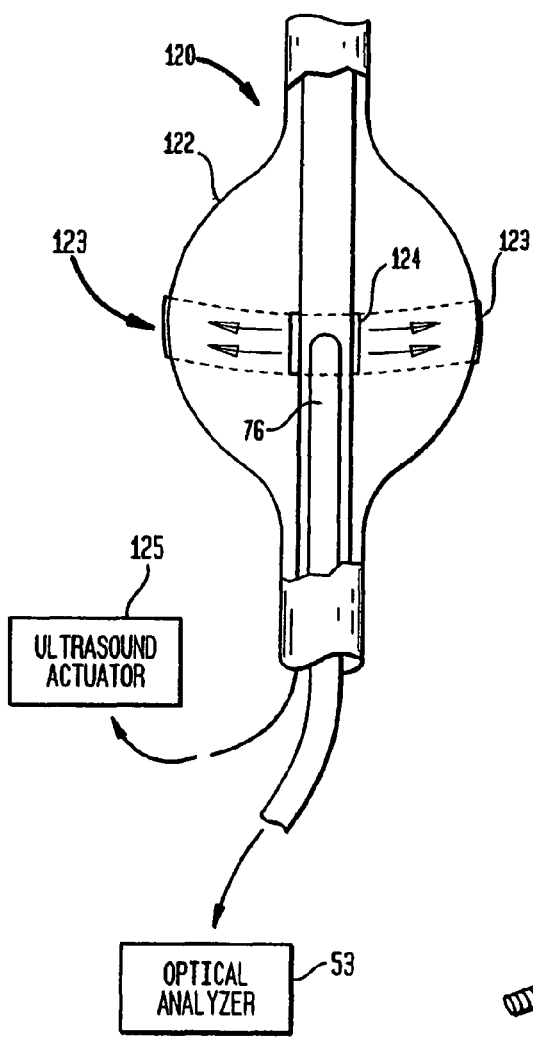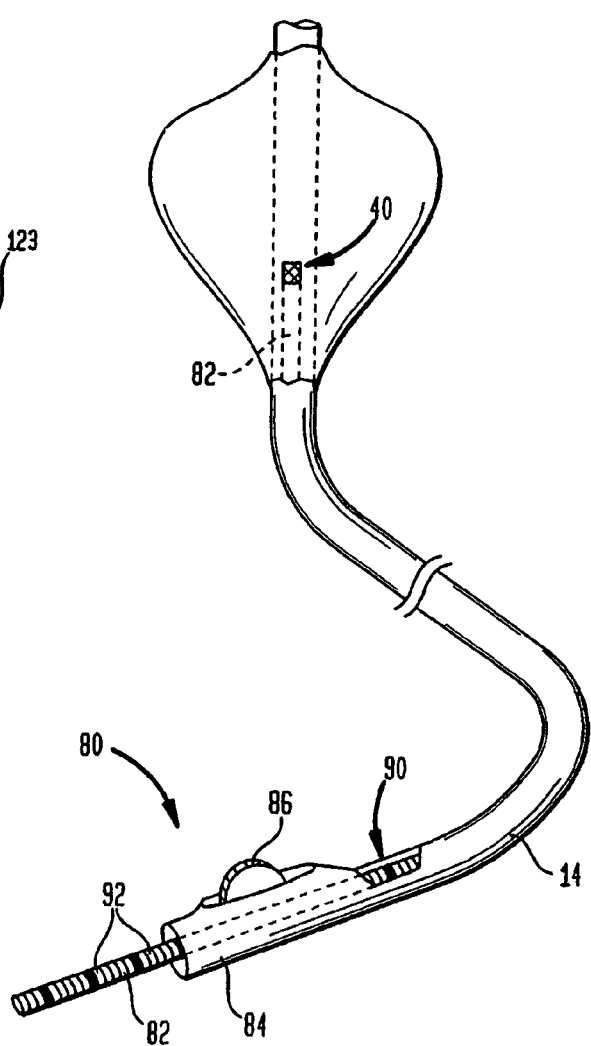

TREATMENT OF ATRIAL FIBRILLATION BY OVERLAPPING CURVILINEAR LESIONS

CROSS-REFERENCE TO RELATED APPLICATIONS

This application is a continuation of U.S. patent application Ser. No. 10/357,156, filed on Feb. 3, 2003, now U.S. Pat. No. 8,025,661, which is a continuation-in-part of U.S. patent application Ser. No. 09/924,394, filed on Aug. 7, 2001, now U.S. Pat. No. 6,579,285 issued Jun. 17, 2003, which is a continuation-in-part of U.S. patent application Ser. No. 09/390,964, filed on Sep. 7, 1999, now U.S. Pat. No. 6,270,492 issued Aug. 7, 2001, which is a continuation-in-part of U.S. patent application Ser. No. 08/991,130, filed on Dec. 16, 1997, now U.S. Pat. No. 5,947,959 issued Sep. 7, 1999, which is a continuation-in-part of U.S. patent application Ser. No. 08/827,631, filed on Apr. 10, 1997, now U.S. Pat. No. 5,908,415 issued Jun. 1, 1999, which is a continuation of U.S. patent application Ser. No. 08/303,605, filed on Sep. 9, 1994, now abandoned.

Additionally, U.S. patent application Ser. No. 10/357,156 is a continuation-in-part of U.S. patent application Ser. No. 09/616,275, filed on Jul. 14, 2000, now U.S. Pat. No. 6,626,900 issued Sep. 30, 2003, which is a continuation-in-part of U.S. patent application Ser. No. 09/602,420 filed on Jun. 23, 2000, now U.S. Pat. No. 6,572,609 issued Jun. 3, 2003, which is a continuation-in-part of U.S. patent application Ser. No. 09/357,355, filed on Jul. 14, 1999, now U.S. Pat. No. 6,423,055 issued Jul. 23, 2002.

The teachings of all of these prior related applications are hereby expressly incorporated by reference.

BACKGROUND OF THE INVENTION

The present invention relates to ablation instruments for the ablation of tissue for the treatment of diseases, and, in particular, to percutaneous instruments employing radiant energy. Methods of ablating tissue using radiant energy are also disclosed. The instruments can be used, for example, in the treatment of cardiac conditions such as cardiac arrhythmias.

Cardiac arrhythmias, e.g., fibrillation, are irregularities in the normal beating pattern of the heart and can originate in either the atria or the ventricles. For example, atrial fibrillation is a form of arrhythmia characterized by rapid randomized contractions of atrial myocardium, causing an irregular, often rapid ventricular rate. The regular pumping function of the atria is replaced by a disorganized, ineffective quivering as a result of chaotic conduction of electrical signals through the upper chambers of the heart. Atrial fibrillation is often associated with other forms of cardiovascular disease, including congestive heart failure, rheumatic heart disease, coronary artery disease, left ventricular hypertrophy, cardiomyopathy, or hypertension.

Various techniques have been proposed for the treatment of arrhythmia. Although these procedures were originally performed with a scalpel, various other techniques have also been developed to form lesions. Collectively, these treatments are referred to as "ablation." In non-surgical ablations, the tissue is treated, generally with heat or cold, to cause coagulation and/or tissue necrosis (i.e., cell destruction). In each of these techniques, cardiac muscle cells are replaced with scar tissue which cannot conduct normal electrical activity within the heart.

For example, the pulmonary vein has been identified as one of the origins of errant electrical signals responsible for triggering atrial fibrillation. In one known approach, circumferential ablation of tissue within the pulmonary veins or at the ostia of such veins has been practiced to treat atrial fibrillation. Similarly, ablation of the region surrounding the pulmonary veins as a group has also been proposed. By ablating the heart tissue (typically in the form of linear or curved lesions) at selected locations, electrical conductivity from one segment to another can be blocked and the resulting segments become too small to sustain the fibrillatory process on their own.

Several types of ablation devices have recently been proposed for creating lesions to treat cardiac arrhythmias, including devices which employ electrical current (e.g., radio-frequency "RF") heating or cryogenic cooling. Such ablation devices have been proposed to create elongated lesions that extend through a sufficient thickness of the myocardium to block electrical conduction. Many of the recently proposed ablation instruments are percutaneous devices that are designed to create such lesions from within the heart. Such devices are positioned in the heart by catheterization of the patient, e.g., by passing the ablation instrument into the heart via a blood vessel, such as the femoral vein.

Devices that rely upon resistive or conductive heat transfer can be prone to serious post-operative complications. In order to quickly perform an ablation with such "contact" devices, a significant amount of energy must be applied directly to the target tissue site. In order to achieve transmural penetration, the surface that is contacted will experience a greater degree of heating (or freezing). For example, in RF heating of the heart wall, a transmural lesion requires that the tissue temperature be raised to about 50° C. throughout the thickness of the wall. To achieve this, the temperature at the contact surface will typically be raised to greater than 100° C. In this temperature regime, there is a substantial risk of tissue destruction (e.g., due to water vaporization micro-explosions or due to carbonization). Charring of the surface of the heart tissue, in particular, can lead to the creation of blood clots on the surface and post-operative complications, including stroke. Even if structural damage is avoided, the extent of the lesion (i.e., the width of the ablated zone) on the surface that has been contacted will typically be greater than necessary.

Ablation devices that do not require direct contact have also been proposed, including acoustic and radiant energy. Acoustic energy (e.g., ultrasound) is poorly transmitted into tissue (unless a coupling fluid is interposed). Laser energy has also been proposed but only in the context of devices that focus light into a scalpel-like point or similar high intensity spot pattern. When the light energy is delivered in the form of a focused spot, the process is inherently time consuming because of the need to expose numerous spots to form a continuous linear or curved lesion.

In addition, existing instruments for cardiac ablation also suffer from a variety of design limitations. The shape of the heart muscle adds to the difficulty in accessing cardiac structures, such as the pulmonary veins on the anterior surface of the heart. Typically, percutaneous devices are positioned with the assistance of a guide wire, which is first advanced into heart. In one common approach, described, for example, in U.S. Pat. No. 6,012,457 issued to Lesh on Jan. 11, 2000 and in International Application Pub. No. WO 00/67656 assigned to Atrionix, Inc., a guide wire or similar guide device is advanced through the left atrium of the heart and into a pulmonary vein. A catheter instrument with an expandable element is then advanced over the guide and into the pulmonary vein where the expandable element (e.g., a balloon) is inflated. The balloon structure also includes a circumferential ablation element, e.g., an RF electrode carried on the outer surface of the balloon, which performs the ablation procedure. The balloon must be large enough and sufficiently rigid to hold the electrode in contact with the inner surface of the pulmonary vein for the length of the procedure. Moreover, because the lesion is formed by an ablation element carried on the surface of the balloon element, the balloon shape inherently limits the locations where a lesion can be formed, i.e., the lesion must be formed at least partially within the pulmonary vein.

In another approach described in U.S. Pat. No. 6,235,025 issued to Swartz et al. on May 22, 2001, a guide wire is again used to percutaneously access a pulmonary vein and a catheter is again slid over the guide to a position within the pulmonary vein. The catheter device includes two spaced-apart balloons, which are inflated in the vein (or in the vein and at its mouth). The space between the two balloons can then be filled with a conductive fluid to delivery RF energy (or, alternatively, ultrasound) to the vein and thereby induce a conduction block in the blood vessel by tissue ablation. With the Swartz et al. device, like the Lesh device, the region where tissue ablation can occur is limited by the design. Because two balloons must seal a space that is then filled with an ablative fluid, the lesion is necessarily formed within the pulmonary vein.

Ablation within the pulmonary vein can result in complications. Overtreatment deep within a vein can result in stenosis (closure of the vein itself), necrosis or other structural damage, any of which can necessitate immediate open chest surgery.

A major limitation in the prior art percutaneous designs is the lack of site selectability. Practically speaking, each prior art percutaneous instrument is inherently limited by its design to forming an ablative lesion at one and only one location. For example, when an expandable balloon carrying an RF heating device on its surface is deployed at the mouth of a vein, the lesion can only be formed at a location defined by the geometry of the device. It is not possible to form the lesion at another location because the heating element must contact the target tissue. Similarly, the above-described tandem balloon device can only form a lesion at a location defined by the space between the balloons that is filled with the ablative fluid.

Another major limitation in prior art percutaneous designs is their inability to accommodate the actual and quite varied geometry of the heart. The inner surface of the atrium is not regular. In particular, the mouths of the pulmonary veins do not exhibit regularity; they often bear little resemblance to conical or funnel-shaped openings. When the expandable, contact heating devices of the prior art encounter irregularly-shaped ostia, the result can be an incompletely formed (non-circumferential) lesion.

Accordingly, a percutaneous ablation device that allows the clinician to select the location of the ablation site would be highly desirable. An instrument that allows a clinician to choose from a number of different lesion locations, especially in creating continuous conduction blocks around pulmonary veins, would satisfy a long felt need in the art.

Moreover, the prior art devices typically can not determine whether continuous circumferential contact has been achieved before heating commences. These devices most often rely on post-ablation electrical mapping to determine whether a circumferential lesion has been formed. If electrical conduction is still present, the encircling lesion is incomplete and the procedure must be repeated or abandoned.

Accordingly, there also exists a need for better surgical ablation instruments that can form lesions with less trauma to the healthy tissue of the heart and greater likelihood of success. A percutaneous system that could determine whether contact has been achieved (or blood has been cleared from the target site) and predict success based on such determinations would represent a significant improvement over the existing designs.

SUMMARY OF THE INVENTION

Ablation methods and instruments are disclosed for creating lesions in tissue, especially cardiac tissue, for treatment of arrhythmias and the like. In one aspect of the invention, percutaneous ablation instruments in the form of coaxial catheter bodies are disclosed having at least one central lumen therein and having one or more balloon structures at the distal end region of the instrument. The balloon structure and catheter bodies are at least partially transmissive to ablative energy. The instruments can further include an energy emitting element, which is independently positionable within the lumen of the instrument and adapted to project ablative energy through a transmissive region of the balloon to a target tissue site. The energy is delivered without the need for contact between the energy emitter and the target tissue because the methods and devices of the present invention do not rely upon conductive or resistive heating. Because the position of the radiant energy emitter can be varied, the clinician can select the location of the desired lesion.

In another aspect of the invention, a cardiac ablation instrument is disclosed having a catheter body adapted for disposition within a heart, and a projection balloon connected to the catheter body and adapted for inflation within the heart to provide a transmission pathway for ablative energy to be delivered to a target tissue site. The cardiac ablation instrument also includes an energy emitter disposable within the balloon at a plurality of locations for the projection of ablative energy through the balloon to form a series of lesions. The energy emitter can be positionable at a plurality of locations along a longitudinal axis within the balloon or it can be adapted for translatory motion to a plurality of locations within the balloon. In one embodiment, the energy emitter is adapted to be positioned at a location where a pulmonary vein extends from an atrium and the series of lesions can encircle an ostium of the pulmonary vein. The energy emitter can project at least a partial ring of radiant ablative energy of variable diameter based on its axial position within the catheter body.

The energy emitter can be adapted to deliver a variety of types of energy. In one embodiment, the energy emitter can be a radiant energy emitter that optionally can include a light transmitting optical fiber that is adapted to receive radiant energy from a light source and a light emitting tip at a distal end of the fiber for emitting light. The light emitting tip can further include a beam forming optical waveguide for projecting an annular beam of light, such that the radiant energy emitter projects a ring of ablative energy of variable diameter based on its axial position within the catheter body, or alternatively, a light diffusing element.

In another embodiment, the energy emitter can include an ultrasound generator, and can generate ultrasound energy at at least one wavelength in the range of about 5 MHz to 20 MHz. Alternatively, the energy emitter can include a microwave generator, a contact heating element located at a distal end of the catheter body, at least one electrode adapted to couple to an electric current source, such as a radiofrequency current source, or a cryogenic ablation element.

The instrument can also have a variety of other features, and can further include a contact sensor, a detector capable of distinguishing at least two wavelengths of reflected light, a light source for generating photoablative radiation at wavelengths in the range of about 800 nm and 1000 nm, and/or a second catheter body with an inner channel configured for coupling to the first catheter body via the channel such that the second catheter body can be passed over the first catheter body into a position within the heart, and/or an inflatable projection balloon which can be deployed to clear blood from a surrounding region within the heart. The catheter body can also be adapted for disposition over a guide wire.

Methods of treating atrial fibrillation are also disclosed herein. In one aspect, the method can include positioning a cardiac ablation instrument in proximity to a target region of a heart, the instrument having a catheter body with at least one lumen therein and an energy emitting element independently positionable within the at least one lumen of the catheter body, and activating the energy emitting element to project ablative energy to form a first lesion in proximity to the target region. The method can further include activating the energy emitting element to project ablative energy to form at least a second lesion in proximity to the target region, the at least second lesion overlapping a portion of the first lesion so as to form a combined lesion that continuously encircles the target region. The energy emitting element can be positioned at a different location after activating the energy emitting element to form the first lesion. In one embodiment, the target region is a pulnonary vein, and the combined lesion circumscribes the pulmonary vein.

The lesions formed can have a variety of configurations, and each lesion can be partially circumferential, in the shape of an arc, or have a similar thickness. Additionally, the position of the energy emitting element can be adjusted to form a lesion having a different thickness than a previous lesion.

The method can also include inflating a projection balloon to clear blood from a transmission pathway between the energy emitting element and a target region of the cardiac tissue. In one embodiment, whether a clear transmission path exists between the energy emitting element and the target region can be determined is based on reflectance measurements by an optical sensor disposed within the ablation instrument by, for example, measuring at least two different wavelengths of reflected light collected by the optical sensor to determine whether a projection path has been established.

A variety of energy emitting elements can be activated to form a lesion on tissue. In one embodiment, activating the energy emitting element can include activating a beam-forming optical waveguide to expose the target region to an annular beam of light energy to induce the combined lesion in cardiac tissue or, alternatively, activating an ultrasound emitting element to expose the target region to acoustic energy to induce photocoagulation of cardiac tissue within the target region. In other embodiments, activating the energy emitting element can include activating a light emitting element to expose the target region to light energy to induce photocoagulation of cardiac tissue within the target region, activating a light emitting element to expose the target region to light energy to induce the combined lesion in the cardiac tissue, activating an ultrasound emitting element to expose the target region to acoustic energy to induce photocoagulation of cardiac tissue within the target region, or activating a radiation emitting element to expose the target region to at least one form of radiant energy selected from the group consisting of microwave, x-ray, gamma-ray and ionizing radiation to induce photocoagulation of cardiac tissue within the target region. By way of non-limiting example, photoablative radiation can be generated at a wavelength in the range of about 800 nm to 1000 nm, and more preferably from about 915 nm to 980 nm.

In another aspect of the invention, generally applicable to a wide range of cardiac ablation instruments, mechanisms are disclosed for determining whether the instrument has been properly seated within the heart, e.g., whether the device is in contact with a pulmonary vein and/or the atrial surface, in order to form a lesion by heating, cooling or projecting energy. This contact-sensing feature can be implemented by an illumination source situated within the instrument and an optical detector that monitors the level of reflected light. Measurements of the reflected light (or wavelengths of the reflected light) can thus be used to determine whether contact has been achieved and whether such contact is continuous over a desired ablation path.

The instruments are especially useful in percutaneous access cardiac surgery for rapid and efficient creation of curvilinear lesions to serve as conduction blocks. The instruments are designed to create lesions in the atrial tissue in order to electrically decouple tissue segments on opposite sides of the lesion while presenting low profiles during percutaneous access and retraction. The instruments of the present invention permit the formation of continuous lesions in the atrial wall tissue of the heart, such that the continuous lesion can surround a organ structure, such as a pulmonary vein, without involving the structure itself.

In one embodiment, a cardiac ablation instrument is disclosed having a catheter body adapted for disposition within a heart. This catheter body has at least one lumen therein and an expandable, energy-transmitting element which can be deployed at the desired location with or without an anchorage element to contact a cardiac structure and establish a transmission pathway. For example, the expandable element can be a projection balloon that is expandable to fill the space between the energy emitter and the target tissue with an energy-transmissive fluid and, thereby, provide a transmission pathway for projected radiant energy. The instrument further includes a radiant energy delivery element movable within the lumen of the catheter body such that it can be disposed at the desired location and deliver radiant energy through a transmissive region of the instrument to a target tissue site. The instrument can further include additional elements, such as fluid delivery ports, to provide a blood-free transmission pathway from the energy emitter to the target tissue.

In another embodiment, a cardiac ablation instrument is disclosed having a catheter body adapted for disposition within a heart and at least one anchorage element which can be deployed at a desired location to contact a cardiac structure and secure the device in place. The instrument again includes a radiant energy delivery element movable within the lumen of the catheter body such that it can be disposed at the desired location and deliver radiant energy through a transmissive region of the instrument to a target tissue site. A projection balloon can again be employed, alone or together with fluid releasing mechanisms, to provide a blood-free transmission pathway from the energy emitter to the tissue target.

Mechanisms are disclosed for determining whether the ablation instruments of the present invention have been properly seated within the heart to form a lesion. For example, if a projection balloon is employed to provide a clear transmission pathway from a radiant energy emitter to the target tissue, the mechanisms of the present invention can sense whether contact has been achieved between the balloon and the target tissue (and/or whether the pathway for projection of radiant energy has been otherwise cleared of obstructions). In one embodiment, this contact-sensing feature can be implemented by an illumination fiber situated within the instrument and an optical detector fiber (or fiber assembly) that monitors the level of reflected light. Measurements of the reflected light (or wavelengths of the reflected light) can thus be used to determine whether contact has been achieved between the projection balloon and the target tissue, whether blood has been cleared from any gaps, and whether a clear and continuous transmission pathway has been established over a desired ablation path.

In a further aspect of the invention, percutaneous instruments are disclosed that can achieve rapid and effective photoablation through the use of tissue-penetrating radiant energy. It has been discovered that radiant energy, e.g., projected electromagnetic radiation or ultrasound, can create lesions in less time and with less risk of the adverse types of surface tissue destruction commonly associated with prior art approaches. Unlike instruments that rely on thermal conduction or resistive heating, controlled penetrating radiant energy can be used to simultaneously deposit energy throughout the full thickness of a target tissue, such as a heart wall, even when the heart is filled with blood. Radiant energy can also produce better defined and more uniform lesions.

The use of radiant energy, in conjunction with catheter structures that are substantially transparent to such radiation at the therapeutic wavelengths, is particularly advantageous in affording greater freedom in selecting the location of the lesion, e.g., the site is no longer limited to the pulmonary vein itself. Because the energy can be projected onto the tissue, a ring-like lesion can be formed in atrial tissue at a distance from the vein, thereby reducing the potential for stenosis and/or other damage to the vein itself.

It has also been discovered that infrared radiation is particularly useful in forming photoablative lesions. In certain preferred embodiments, the instruments emit radiation at a wavelength in a range from about 800 nm to 1000 nm, and preferably at a wavelength in a range of about 915 nm to 980 nm. Radiation at a wavelength of about 915 nm or about 980 nm is commonly preferred, in some applications, because of the optimal absorption of infrared radiation by cardiac tissue at these wavelengths.

In another embodiment, focused ultrasound energy can be used to ablate cardiac tissue. In certain preferred embodiments, an ultrasound transducer can be employed to transmit frequencies within the range of about 5 MHz to 20 MHz, and preferably in some applications within the range of about 7 MHz to 10 MHz. In addition, the ultrasonic emitter can include focusing elements to shape the emitted energy into an annular beam.

However, in certain applications, other forms of radiant energy can also be useful including, but not limited to, other wavelengths of light, other frequencies of ultrasound, x-rays, gamma-rays, microwave radiation and hypersound.

In the case of radiant light, the energy delivering element can include a light transmitting optical fiber adapted to receive ablative radiation from a radiation source and a light emitting tip at a distal end of the fiber for emitting radiation. The light delivering element can be slidably disposed within an inner lumen of the catheter body and the instrument can further include a translatory mechanism for disposing the tip of the light delivering element at one or more of a plurality of locations with the catheter. Moreover, by moving the energy-projecting tip assembly within the catheter, the diameter of the projected ring of energy can be readily varied, thereby permitting the clinician control over the location (and size) of the lesion to be formed.

Optionally, a fluid can be disposable between the radiant energy delivery element and the target region. In one preferred embodiment a "projection balloon" is filled with a radiation-transmissive fluid so that radiant energy from the energy emitter can be efficiently passed through the instrument to the target region. The fluid can also be used to cool the energy emitter. In certain applications, it can be desirable to use deuterium oxide (so-called "heavy water") as a balloon-filling fluid medium because of its loss of absorption characteristics vis-à-vis infrared radiation. In other applications, the inflation fluid can be water or saline.

It can also be desirable to employ an "ablative fluid" outside of the instrument (e.g., between the balloon and the target region) to ensure efficient transmission of the radiant energy when the instrument is deployed. An "ablative fluid" in this context is any fluid that can serve as a conductor of the radiant energy. This fluid can be a physiologically compatible fluid, such as saline, or any other non-toxic aqueous fluid that is substantially transparent to the radiation. In one preferred embodiment, the fluid is released via one or more exit ports in the housing and flows between the projection balloon and the surrounding tissue, thereby filling any gaps where the balloon does not contact the tissue. The fluid can also serve an irrigation function by displacing any blood within the path of the radiant energy, which could otherwise interfere because of the highly absorptive nature of blood with respect to radiant light energy.

Similarly, if the radiant energy is acoustic, aqueous coupling fluids can be used to ensure high transmission of the energy to the tissue (and likewise displace blood that might interfere with the radiant acoustic energy transfer).

The ablative fluids of the present invention can also include various other adjuvants, including, for example, photosensitizing agents, pharmacological agents, and/or analgesics.

As noted above, contact sensing mechanisms are also disclosed to assist the clinician in selecting the location of the lesion and in ensuring a selected location will result in the formation of a continuous (e.g., vein encircling) lesion. In one embodiment, the sensor employs a plurality of reflection sensors that indicate whether or not a clear transmission pathway has been established (e.g., whether the projection balloon is properly seated and any gaps in contact have been filled by an ablative fluid).

The coaxial catheter instruments disclosed herein are of particular use in percutaneous applications whereby a balloon catheter with an ablative light or ultrasound projecting assembly can be disposed within a patient's heart. In another aspect of the invention, dual, coaxial balloon structures are disclosed, having both a projection balloon and an anchoring balloon to assist in the proper disposition of the instrument.

In the dual, coaxial, catheter embodiment, the catheter instrument can include at least one expandable anchor balloon disposed about, or incorporated into, an inner catheter body designed to slide over a guidewire. This anchor balloon is generally or substantially sealed and serves to position the device within a lumen, such as a pulmonary vein. The anchor balloon structure, when filled with fluid, expands and is engaged in contact with tissue, e.g., the inner surface of a pulmonary vein.

A second catheter carrying the projection balloon can then be slid over the first (anchor balloon) catheter body and inflated within the heart, e.g., within the left atrium and adjacent to the pulmonary vein where the anchor balloon has already been placed. The expanded projection balloon thus defines a staging from which to project radiant energy in accordance with the invention. An energy emitting element can then be introduced via an inner lumen to project radiant energy, e.g., infrared light or ultrasound, through the coaxial catheter bodies and the projection balloon to form a lesion at the target treatment site. The instrument can also include an irrigation mechanism for delivery of an ablative fluid at the treatment site. In one embodiment, irrigation is provided by a sheath, partially disposed about the projection balloon, and provides irrigation at a treatment site (e.g., so that blood can be cleared from an ablation site).

Both the anchor and projection balloon structures can be deflated by applying a vacuum which removes the fluid from the balloons. Once fully deflated, the coaxial instrument can be removed from the body lumen either as an ensemble, or as individual elements (starting with the innermost element). Alternatively, the energy delivery element can be removed (via an inner lumen balloon structure), followed by the projection balloon catheter and then the anchor balloon catheter.

The invention can also be used in conjunction with one or more mapping catheters. For example the guide wire element (and/or the anchorage balloon catheter) can be removed and replaced with a mapping catheter before and/or after the lesion is formed to determine whether the ablation has been successful in stopping errant electrical signals from propagating in the atrial wall tissue.

The present invention also provides methods for ablating tissue. One method of ablating tissue comprises positioning a radiant energy emitting element at a distance from a target region of tissue, providing a blood-free transmission pathway between the emitter and the target region, and then projecting radiant energy to expose the target region and induce a lesion.

In one method according to the invention, a guide wire can be inserted into the femoral vein and advanced through the inferior vena cava, and into the right atrium, or, if required, guided into the left atrium via an atrial septal puncture. In either event, the guide wire can be advanced until it enters a pulmonary vein. The first catheter body can then be slid over the guide wire until its anchorage element, e.g., the anchor balloon, is likewise advanced into the pulmonary vein. The anchor balloon can then be inflated via an inflation fluid to secure the first catheter body. Next, a second catheter body can be advanced, coaxially, over the first catheter body, carrying a projection balloon to the treatment site. Once the projection balloon is proximate to the target tissue ablation site, it can likewise be inflated. In addition, a solution can be injected through the instrument to force blood and/or body fluids away from the treatment site.

The guide wire can then be removed and replaced with the radiant energy emitter, which is positioned to deliver radiant energy through the projection balloon to induce tissue ablation. The methods of the present invention can further include a position sensing step to assist the clinician in selecting the location of the lesion and in ensuring a selected location will result in the formation of a continuous (e.g., vein encircling) lesion. In one embodiment, one or more reflection sensors can be activated to determine whether a clear transmission pathway has been established (e.g., whether the projection balloon is properly seated and any gaps in contact have been filled by an ablative fluid).

Following the ablation procedure, the radiant energy emitter can be removed from the central lumen of the first catheter body. The anchor balloon can then be deflated by applying a vacuum that removes the inflation fluid from the balloon. A syringe or other known methods can be used to remove the fluid. In one embodiment, the anchor balloon can be deflated first and removed along with the first (inner) catheter body. The first catheter body can then be replaced with a mapping catheter. Once the mapping electrode is advanced into the pulmonary vein, the projection balloon can be likewise deflated and the second catheter body removed, thus leaving only the mapping catheter in place. The mapping catheter can then be activated to determine whether a conduction block has been achieved. If the ablation is successful, the mapping catheter can be removed. If conduction is still present, the procedure can be repeated, for example, by reintroducing the second catheter body, followed by removal of the mapping catheter, and repositioning the anchor balloon and the radiant energy emitter.

BRIEF DESCRIPTION OF THE DRAWINGS

The invention will be more fully understood from the following detailed description taken in conjunction with the accompanying drawings, in which like reference numerals designate like parts throughout the figures, and wherein:

FIG. 1 is a schematic, cross-sectional view of a coaxial catheter ablation instrument according to the invention;

FIG. 2 is a schematic illustration of an initial step in performing ablative surgery with radiant energy according to the invention, in which a guide wire is introduced into a heart and passed into a pulmonary vein;

FIG. 3 is a schematic illustration of another step in performing ablative surgery with radiant energy according to the invention, in which a first catheter, carrying an anchoring balloon structure, is slid over the guide wire;

FIG. 4 is a schematic illustration of a further step in performing ablative surgery according to the invention, in which an anchoring balloon structure is inflated;

FIG. 9 is a schematic illustration of an alternative step in performing ablative surgery according to the invention, in which the radiant energy emitter is positioned to form a lesion at a different defined location;

FIG. 10 is a schematic illustration of a further step in performing ablative surgery according to the invention, in which the radiant energy emitter is removed and the anchor balloon element of the first catheter is deflated to permit removal of the first catheter body;

FIG. 17 is a schematic illustration of one embodiment of a radiant light energy emitter according to the invention;

FIG. 18 is a schematic illustration of another embodiment of a radiant light energy emitter according to the invention;

FIG. 23B is a schematic view of an ultrasound heating ablation device employing the contacting sensing apparatus of the present invention; and FIG. 24 is a schematic illustration of a mechanism for positioning the radiant energy emitter at a selected location relative to the target tissue region.

DETAILED DESCRIPTION

Figure 5:
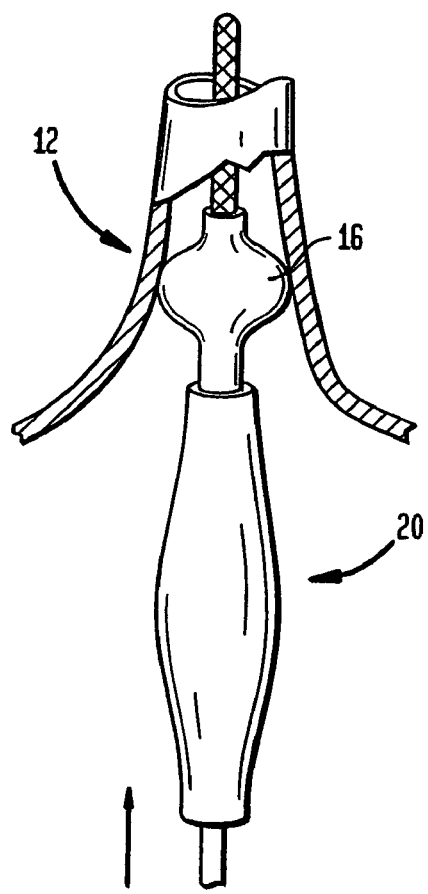
FIG. 5 is a schematic illustration of a further step in performing ablative surgery according to the invention, in which a second catheter, carrying a projection balloon element, is slid over the first catheter body.

FIG. 1 provides a schematic, cross-sectional view of a coaxial catheter ablation instrument 10 according to the invention, including a first, inner catheter 12 having an elongate body 14 and an anchor balloon 16 inflatable via one or more ports 18. A fluid for inflating the anchor balloon can be delivered through a passageway (not shown) within the elongate body or via one or more of the lumens of the device, as discussed in more detail below. The device can further include a second, coaxial, outer catheter 20 having an elongate body 24 and a projection balloon 26 inflatable via one or more ports 22. The instrument is preferably designed such that upon anchorage of the anchor balloon 16 within the heart (e.g., within a pulmonary vein), the projection balloon can be inflated such that a shoulder portion 50 of the balloon 26 will be urged into close proximity with a target region 52 of cardiac tissue (e.g. an annular region of the atrial heart wall surrounding the ostium of a pulmonary vein).

The instrument can also include one or more ports 36 (in fluid communication with either the first catheter 12 or second catheter 20, or both) for delivering ablative fluid to the target region. Preferably, the ablative fluid is an energy transmissive medium, which helps deliver light, radiation, or acoustic energy from a radiant energy source to a target tissue region. The ablative fluid also serves to clear blood from the vicinity of the instrument and compensate for irregularities in the shape of the heart that might otherwise compromise the seating of the instrument. The ablative fluid thus provides a clear transmission pathway external to the balloon.

Within the projection balloon 26 a radiant energy emitter 40 can be disposed remotely from the target tissue (e.g., within a central lumen of the coaxial catheters 12, 20). In one embodiment, the radiant energy source includes at least one optical fiber 42 coupled to a distal light projecting optical element 43, which cooperate to project ablative light energy through the instrument to the target site. The catheter bodies, projection balloon, and inflation/ablation fluids are all preferably substantially transparent to the radiant energy at the selected wavelength to provide a low-loss transmission pathway from the projection element 44 to the target.

FIG. 2 is a schematic illustration of an initial step in performing ablative surgery with radiant energy according to the invention, in which a guide wire 6 is introduced into a heart 2 and passed into a pulmonary vein 4. FIG. 3 illustrates the next step in performing ablative surgery according to the invention, in which a first catheter 12, carrying an anchoring balloon structure 16, is slid over the guide wire 6. This first catheter 12 can further include at least one internal fluid passageway (not shown) for inflation of the balloon 12, which is sealed to the body of the catheter 14 by distal seal 15 and proximal seal 17, such that the introduction of an inflation fluid into the balloon 16 can inflate the balloon as shown in FIG. 4. For further details on anchoring balloon structures, see commonly owned U.S. patent application Ser. No. 09/616,303 filed Jul. 14, 2000 and now U.S. Pat. No. 6,796,972 issued on Sep. 28, 2004, entitled "Catheter Anchoring Balloon Structure with Irrigation," the disclosures of which are hereby incorporated by reference.

FIG. 5 is a schematic illustration of a further step in performing ablative surgery according to the invention, in which a second catheter 20, likewise having a elongated body 24 and carrying a projection balloon element 26, is slid over the first catheter body 14. This second catheter 20 also includes at least one internal fluid passageway (not shown) for inflation of the balloon 26, which is sealed to the body 24 of the catheter 20 by distal seal 21 and proximal seal 22, such that the introduction of an inflation fluid into the balloon 26 can inflate the balloon as shown in FIG. 6.

Figure 6:
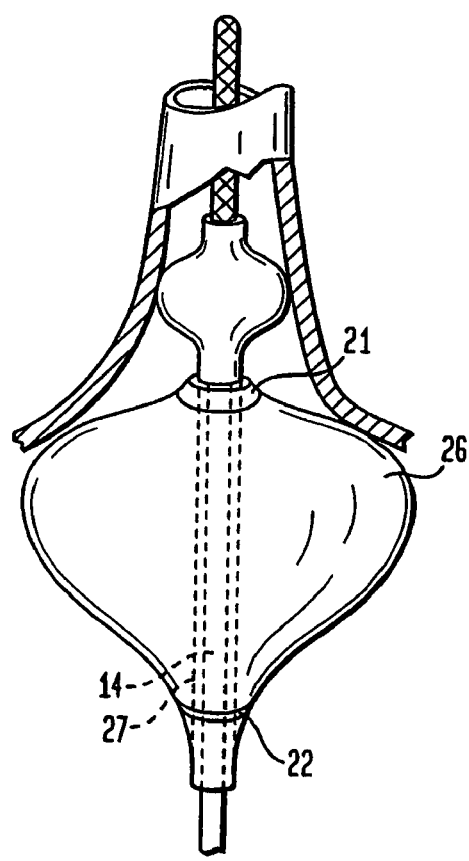
FIG. 6 is a schematic illustration of a further step in performing ablative surgery according to the invention, in which the projection balloon element of the second catheter is inflated to define a projection pathway for radiant energy ablation of cardiac tissue.

Thus, FIG. 6 illustrates how the projection balloon 26 of the second catheter 20 can be deployed and inflated to define a projection pathway for radiant energy ablation of cardiac tissue. Second catheter body 24 has an inner lumen 27 sized to pass over the inner catheter body 14. Once it is positioned in the heart, the projection balloon of the second catheter is then inflated. The expanded projection balloon defines a staging through which radiant energy can be projected in accordance with the invention. In one preferred embodiment, the projection balloon is filled with a radiation-transmissive fluid so that radiant energy from an energy emitter can be efficiently passed through the instrument to a target region of cardiac tissue.

The projection balloons described herein can be preshaped to form a parabolic like shape. This can be accomplished, for example, by shaping and melting a TEFLON® film in a preshaped mold to effect the desired form. The projection balloons and sheaths of the present invention can be made, for example, of thin wall polyethylene teraphthalate (PET) with a thickness of the membranes of about 5-50 micrometers.

It should be noted that it is not necessary (and in some cases, not desirable) for the projection balloon 26 to contact the target tissue in order to ensure radiant energy transmission. One purpose of the projection balloon is simply to clear a volume of blood away from the path of the energy emitter. With reference again to FIG. 1, an ablative fluid 29 can be employed outside of the instrument (e.g., between the balloon 26 and the target region 52) to ensure efficient transmission of the radiant energy when the instrument is deployed. The ablative fluid in this context is any fluid that can serve as a conductor of the radiant energy. This ablative fluid can be a physiologically compatible fluid, such as saline, or any other non-toxic aqueous fluid that is substantially transparent to the radiation. As shown in FIG. 1, the fluid 29 can be released via one or more exit ports 36 in the first catheter body 14 (and/or second catheter body 24) to flow between the projection balloon 26 and the surrounding tissue, thereby filling any gaps where the balloon 26 does not contact the tissue. The fluid 29 can also serve an irrigation function by displacing any blood within the path of the radiant energy, which could otherwise interfere with the radiant light energy transmission to the target region 52.

For alternative designs for delivery of ablative and/or irrigation fluids, see commonly-owned, U.S. patent application Ser. No. 09/660,601, filed Sep. 13, 2000 and now U.S. Pat. No. 6,605,055 issued Aug. 12, 2003, entitled "Balloon Catheter with Irrigation Sheath," the disclosures of which are hereby incorporated by reference. For example, in one embodiment described in patent application Ser. No. 09/660,601, the projection balloon can be partially surrounded by a sheath that contains pores for releasing fluid near or at the target ablation site. A person having ordinary skill in the art will readily appreciate that such pores can vary in shape, size, and/or quantity, and that placement of the fluid ports of various designs can be varied to provide a desired amount of fluid to the treatment site.

Figure 7:
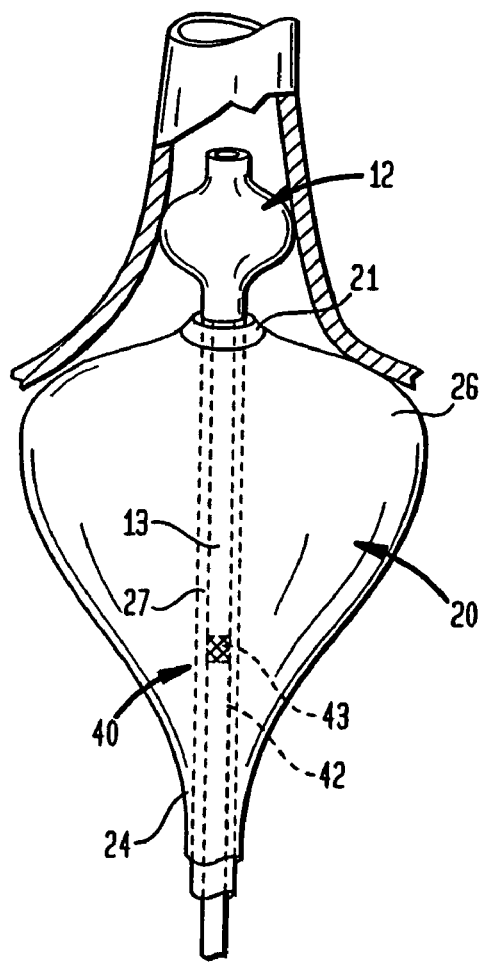
FIG. 7 is a schematic illustration of a further step in performing ablative surgery according to the invention, in which the guide wire is removed and replaced by a radiant energy emitter located remote from the lesion site but in a position that permits projection of radiant energy onto a target region of the heart.

FIG. 7 is a schematic illustration of a further step in performing ablative surgery according to the invention, in which the guide wire is removed and replaced by a energy emitter 40 located remote from the desired lesion site 52 but in a position that permits projection of radiant energy onto a target region of the heart. The energy emitter can be introduced into the instrument via the lumen 13 of the inner catheter. In the illustrated embodiment, the energy emitter 40 is a radiant energy emitter and includes at least one optical fiber 42 coupled to a distal light projecting, optical element 43, which cooperate to project ablative light energy through the instrument to the target site. In one preferred embodiment, optical element is a lens element capable of projecting an annular (ring-shaped) beam of radiation, as described in more detail in commonly owned U.S. Pat. No. 6,423,055 issued Jul. 22, 2002, herein incorporated by reference.

Figure 8:
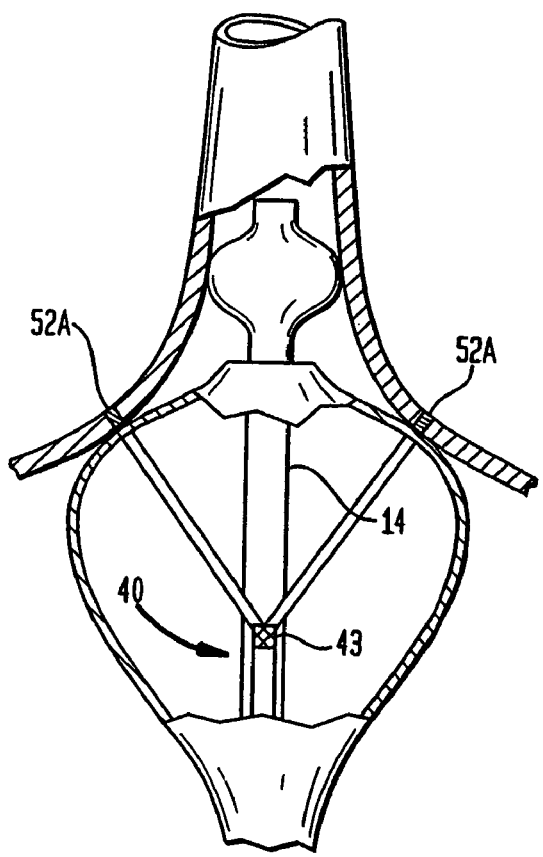
FIG. 8 is a schematic illustration of a step in performing ablative surgery according to the invention, in which the radiant energy emitter is positioned to form a lesion at a defined location.

FIGS. 8 and 9, taken together, illustrate an advantageous feature of the present invention, namely, the ability to select the location of a lesion independent of the instrument design. Because the radiant energy emitter does not require contact with a target tissue region and is, in fact, decoupled from the rest of the instrument, the present invention permits the clinician to select a desired target region by simply moving the emitter (e.g., within the lumen 14 of the first catheter 12). As shown in FIG. 8, the radiant energy emitter can be positioned to form a wide circumferential lesion (when the shape of the pulmonary vein ostium warrants such a lesion) by positioning the radiant energy emitter at the rear of the projection balloon—at a distance from the target tissue. Alternatively, a smaller diameter lesion can be formed by positioning the radiant energy emitter closer to the front of the projection balloon, as shown in FIG. 9. Such a lesion can be preferable when the geometry of the vein ostium presents a more gradual change in diameter, as shown. It should be appreciated that it may be desirable to change the intensity of the emitted radiation depending upon the distance it must be projected; thus a more intense radiant energy beam may be desirable in the scheme illustrated in FIG. 8 versus that shown in FIG. 9. The energy emitter 40 and catheter body 24 can each include one or more markers (shown schematically as elements 33 and 35, respectively) to aid in determining the location or tracking movements of the elements. Markers 33 and 35, for example, can be radiopaque lines that can be visualized fluoroscopically. Various other marker mechanisms, such as magnetic, capacitive, or optical markers, can also be used.

FIG. 10 is a schematic illustration of a further step in performing ablative surgery according to the invention, in which the radiant energy emitter 40 (shown in FIGS. 7-9) has been removed and the anchor balloon element 16 of the first catheter 12 is deflated to permit removal of the first catheter body 14.

Figure 11:
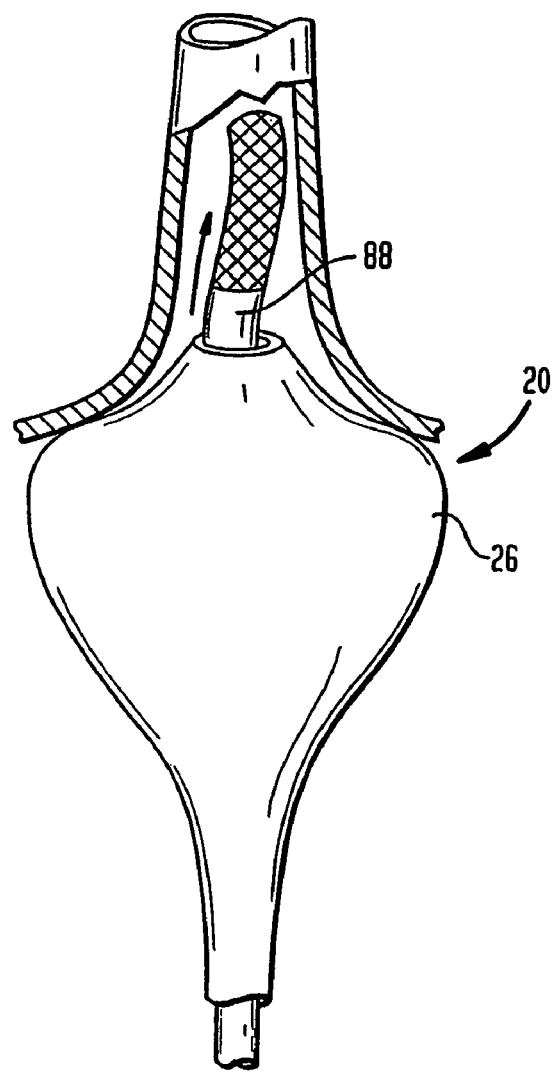
FIG. 11 is a schematic illustration of a further step in performing ablative surgery according to the invention, in which the first catheter is replaced by a mapping electrode.

In FIG. 11, the first catheter is replaced by a mapping electrode catheter 88 via, for example, the central lumen of the second catheter 20. However, it should be appreciated that more than one lumen can be used to provide separate pathways for these instruments. Once the mapping electrode is positioned within a pulmonary vein, an electrical pulse can be applied to determine whether the lesion formed by the radiant energy emitter (as described above) is sufficient to serve as a conduction block.

Figure 12:
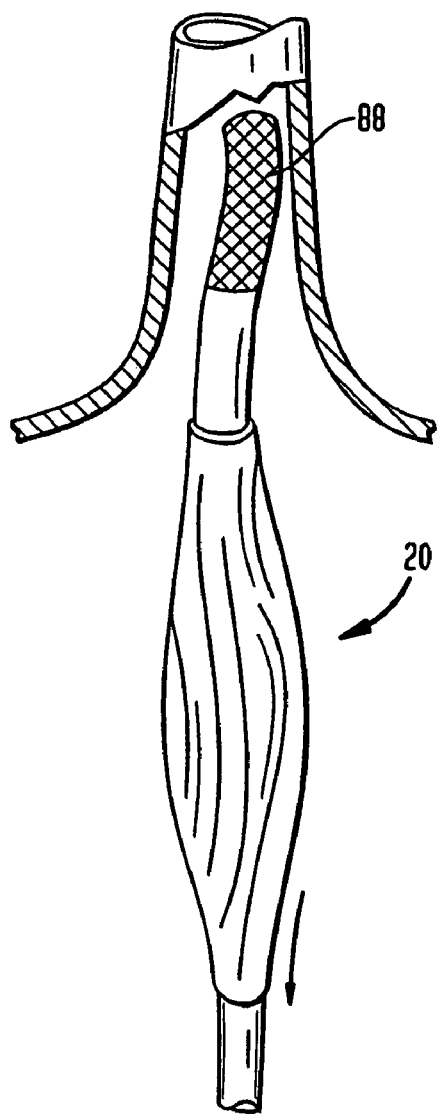
FIG. 12 is a schematic illustration of a further step in performing ablative surgery according to the invention, in which the projection balloon is deflated and removed while the mapping electrode remains in place to verify the formation of an electrical conduction block.

FIG. 12 is a schematic illustration of a final step in which the projection balloon is deflated and removed while the mapping electrode remains in place to verify the formation of an electrical conduction block. Various techniques for conducting such tests are known by those skilled in the art. In one simple approach, a voltage pulse is applied by a coronary sinus catheter. The mapping catheter's electrode is touched to the inner wall of the pulmonary vein. If no signal (or a substantially attenuated signal) is detected, a conduction block can thereby be confirmed. It should also be appreciated that the mapping electrode can in some instances be used even before the projection and/or anchor balloons are removed.

Figure 13:
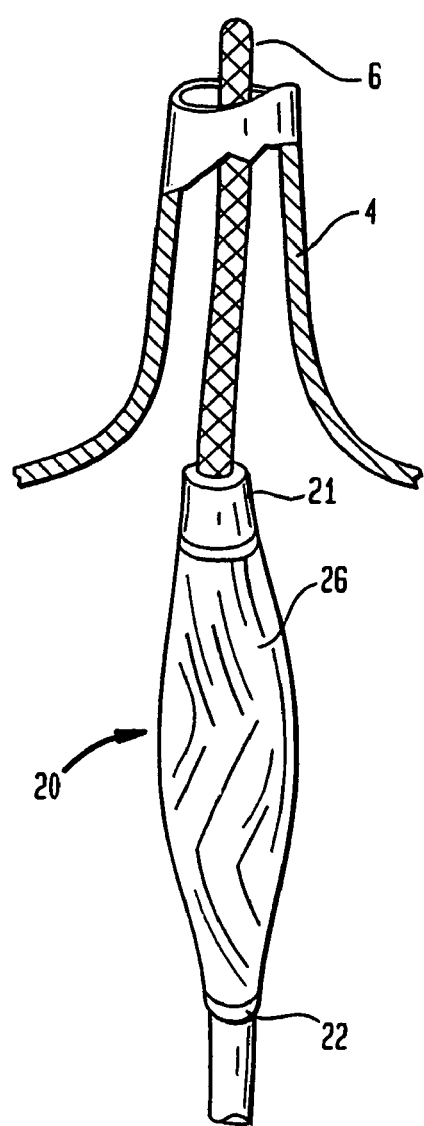
FIG. 13 is a schematic illustration of an alternative approach to ablative surgery with radiant energy according to the invention, in which a catheter carrying a projection balloon structure is slid over a guide wire without first introducing an anchoring balloon catheter.

FIG. 13 is a schematic illustration of an alternative method of performing ablative surgery with radiant energy according to the invention without the need for an anchoring balloon. As shown in FIG. 13, a guide wire 6 can again be introduced into a heart and passed into a pulmonary vein 4. A catheter 20 carrying projection balloon structure 26 is slid over the guide wire 6. This catheter 20 can further include at least one internal fluid passageway (not shown) for inflation of the balloon 26, which is sealed to the body of the catheter 20 by distal seal 21 and proximal seal 22, such that the introduction of an inflation fluid into the balloon 26 can inflate the balloon.

Figure 14:
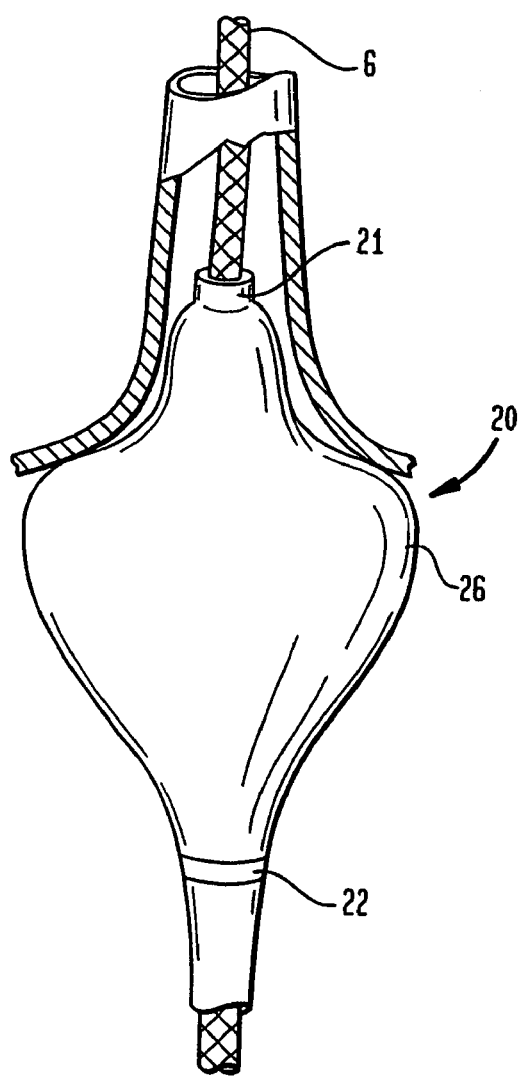
FIG. 14 is a schematic illustration of a further step in performing ablative surgery with the embodiment illustrated in FIG. 13, in which the projection balloon element is inflated to define a projection pathway for radiant energy ablation of cardiac tissue.

FIG. 14 illustrates how the projection balloon 26 can then be inflated to define a projection pathway for radiant energy ablation of cardiac tissue. The expanded projection balloon defines a staging through which radiant energy can be projected in accordance with the invention. In one preferred embodiment, the projection balloon is filled with a radiation-transmissive fluid so that radiant energy from an energy emitter can be efficiently passed through the instrument to a target region of cardiac tissue.

The projection balloons described herein can be preshaped to form various shapes (e.g., to assist in seating the instrument at the mouth of a pulmonary vein or at other anatomically defined regions of the heart). As noted above, this can be accomplished, for example, by shaping and melting a TEFLON® film in a preshaped mold to effect the desired form. Again, the projection balloons can be made, for example, of thin wall polyethylene teraphthalate (PET) with a thickness of the membranes of about 5-50 micrometers.

One purpose of the projection balloon is to clear a volume of blood away from the path of the energy emitter. Towards this end, the instrument can further include a fluid releasing mechanism in the form of one or more fluid ports (or a sheath that contains pores for releasing fluid) near or at the target ablation site. Again, the released fluid can serve as an ablative fluid by clearing a transmission pathway for radiant energy.

Figure 15:
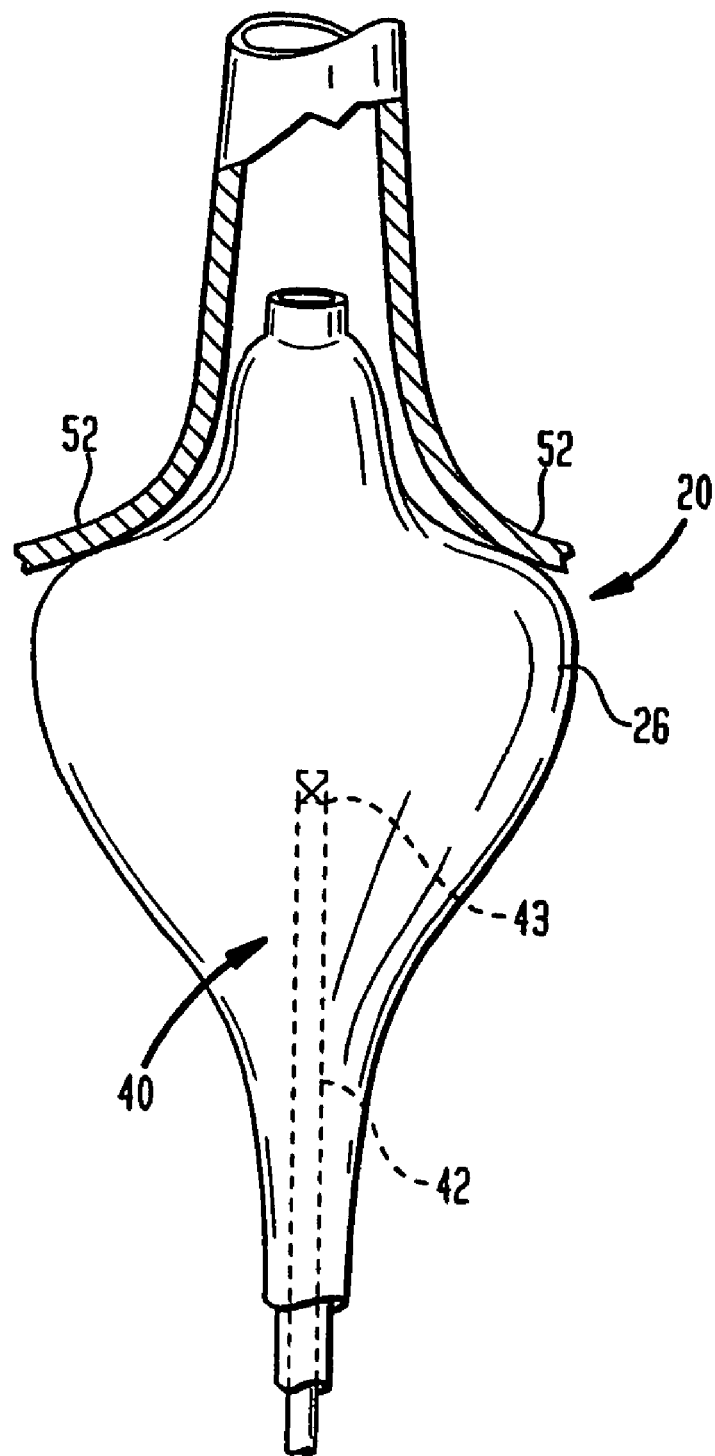
FIG. 15 is a schematic illustration of a further step in performing ablative surgery with the embodiment illustrated in FIG. 13, in which the guide wire is removed and replaced by a radiant energy emitter located remote from the lesion site but in a position that permits projection of radiant energy onto a target region of the heart.

FIG. 15 is a schematic illustration of a further step in performing ablative surgery with the device of FIGS. 13-14, in which the guide wire is removed and replaced by a radiant energy emitter 40 located remote from the desired lesion site 52 but in a position that permits projection of radiant energy onto a target region of the heart. In the illustrated embodiment, the radiant energy emitter 40 includes at least one optical fiber 42 coupled to a distal light projecting, optical element 43, which cooperate to project ablative light energy through the instrument to the target site. In one preferred embodiment, the optical element is again a lens element capable of projecting an annular (ring-shaped) beam of radiation, as described in more detail in commonly owned U.S. Pat. No. 6,423,055 issued Jul. 22, 2002, herein incorporated by reference. Alternatively, the radiant energy emitter can be an ultrasound or microwave energy source, as described in more detail below (in connection with FIGS. 19-20).

Figure 16:
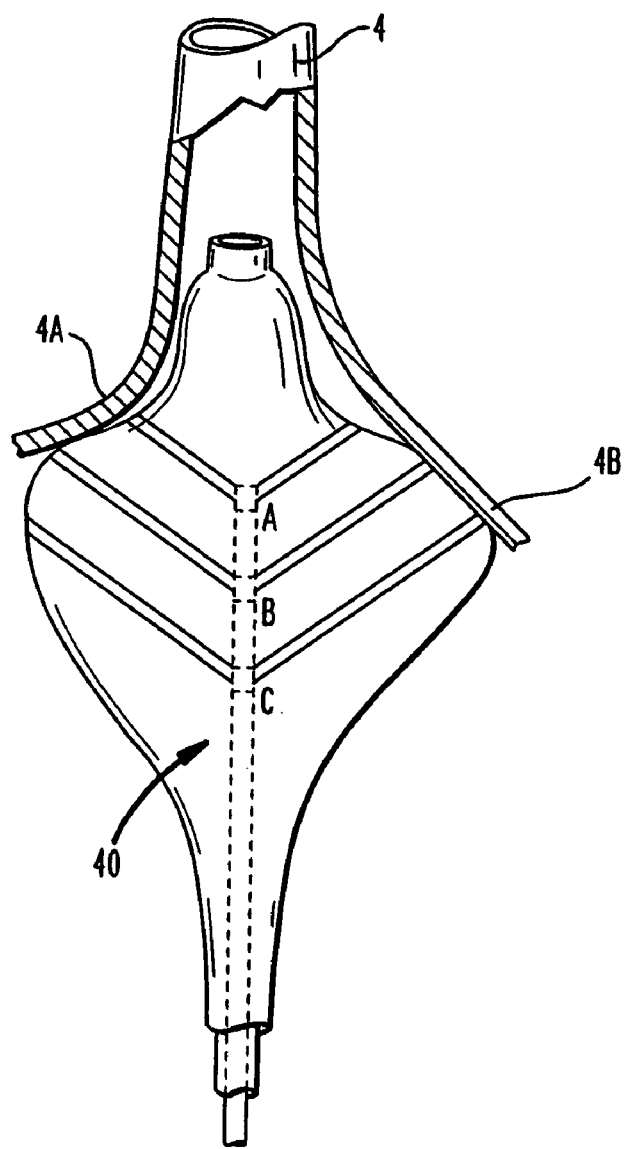
FIG. 16 is a schematic illustration of a system according to the invention in which an asymmetric vein mouth is encountered and further showing how the position of the radiant energy emitter can be adjusted to sense contact and select a location.

FIG. 16 further illustrates the unique utility of the multi-positionable, radiant energy ablation devices of the present invention in treating the complex cardiac geometries that are often encountered. As shown in the figure, the mouths of pulmonary veins typically do not present simple, funnel-shaped, or regular conical surfaces. Instead, one side of the ostium 4B can present a gentle sloping surface, while another side 4A presents a sharper bend. With prior art, contact-heating, ablation devices, such geometries will result in incomplete lesions if the heating element (typically a resisting heating band on the surface of an expandable element) can not fully engage the tissue of the vein or ostium. Because the position of the heating band of the prior art devices is fixed, when it does not fully contact the target tissue, the result is an arc, or an incompletely formed ring-type, lesion that typically will be insufficient to block conduction.

FIG. 16 illustrates how the slidably positionable energy emitters of the present invention can be used to avoid this problem. Three potential positions of the emitter 40 are shown in the figure (labeled as "A", "B" and "C"). As shown, positions A and C may not result in optimal lesions because of gaps between the balloon and the target tissue. Position B, on the other hand, is preferable because circumferential contact has been achieved. Thus, the independent positioning of the energy source relative to the balloon allows the clinician to "dial" an appropriately ring size to meet the encountered geometry. (Although three discrete locations are shown in FIG. 16, it should be clear that emitter can be positioned in many more positions and that the location can be varied in either discrete intervals or continuously, if so desired.)

Figure 16A:
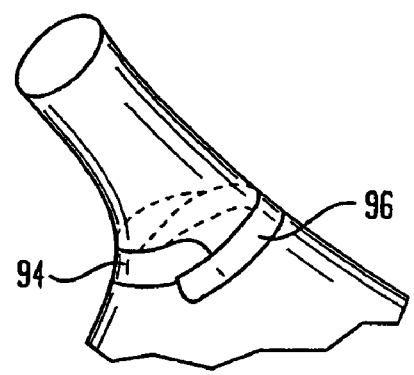
FIG. 16A illustrates how a continuous, vein-encircling lesion can be formed by two partially-encircling lesions.

Moreover, in some instances the geometries of the pulmonary vein (or the orientation of the projection balloon relative to the ostium) may be such that no single annular lesion can form a continuous conduction block. Again, the present invention provides a mechanism for addressing this problem by adjustment of the location of the energy emitter to form two or more partially circumferential lesions. As shown in FIG. 16A, the devices of the present invention can form a first lesion 94 and a second lesion 96, each in the form of an arc or partial ring. Because each lesion has a thickness (dependent largely by the amount of energy deposited into the tissue) the two lesions can axially combine, as shown, to form a continuous encircling or circumscribing lesion that blocks conduction.

FIG. 17 is a schematic illustration of one embodiment of a radiant energy emitter 40A according to the invention. In one preferred embodiment, the radiant energy is electromagnetic radiation, e.g., coherent or laser light, and the energy emitter 40A projects a hollow cone of radiation that forms an annular exposure pattern upon impingement with a target surface. For example, as shown in FIG. 17, the radiant energy emitter 40A can include an optical fiber 42 in communication with an annulus-forming optical waveguide 44 having a concave interior boundary or surface 45. The waveguide 44 passes an annular beam of light to a graded intensity (GRIN) lens 46, which serves to collimate the beam, keeping the beam width the same, over the projected distance. The beam that exits from the distal window 48 of energy emitter 40A will expand (in diameter) over distance, but the energy will remain largely confined to a narrow annular band. Generally, the angle of projection from the central axis of the optical fiber 42 or waveguide 44 will be between about 20 and 45 degrees.

The diameter of the annular beam of light will be dependent upon the distance from the point of projection to point of capture by a surface, e.g., a tissue site, e.g., an interstitial cavity or lumen. Typically, when the purpose of the radiant energy projection is to form a transmutably cardiac lesion, e.g., around a pulmonary vein, the diameter of the annular beam will be between about 10 mm and 33 mm, preferably greater than about 10 mm, greater than about 15 mm, greater than about 20 mm, and most preferably, greater than or equal to about 23 mm. Typically, the angle of projected annular light is between about 20 and 45 degrees, preferably between about 17 and 30 degrees, and most preferably between about 16 and 25 degrees.

Preferred energy sources for use with the percutaneous ablation instruments of the present invention include laser light in the range between about 200 nanometers and 2.5 micrometers. In particular, wavelengths that correspond to, or are near, water absorption peaks are often preferred. Such wavelengths include those between about 805 nm and 1060 nm, preferably between about 900 nm and 1000 nm, and most preferably, between about 915 nm and 980 nm. In a preferred embodiment, wavelengths around 915 nm or around 980 nm are used during endocardial procedures. Suitable lasers include excimer lasers, gas lasers, solid state lasers and laser diodes. One preferred AlGaAs diode array, manufactured by Spectra Physics, Tucson, Ariz., produces a wavelength of 980 nm.

The optical waveguides, as described in above, can be made from materials known in the art such as quartz, fused silica, or polymers such as acrylics. Suitable examples of acrylics include acrylates, polyacrylic acid (PAA) and methacrylates, polymethacrylic acid (PMA). Representative examples of polyacrylic esters include polymethylacrylate (PMA), polyethylacrylate and polypropylacrylate. Representative examples of polymethacrylic esters include polymethylmethacrylate (PMMA), polyethylmethacrylate and polypropylmethacrylate. In one preferred embodiment, the waveguide 44 is formed of quartz and fused to the end face of fiber 42.

Internal shaping of the waveguide can be accomplished by removing a portion of material from a unitary body, e.g., a cylinder or rod. Methods known in the art can be utilized to modify the waveguide to have tapered inner walls, e.g., by grinding, milling, ablating, etc. In one approach, a hollow polymeric cylinder, e.g., a tube, is heated so that the proximal end collapses and fuses together, forming an integral proximal portion which tapers to the distal end of the waveguide. In another approach, the conical surface 45 can be formed in a solid quartz cylinder or rod by drilling with a tapered bore.

The waveguide 44 can be optically coupled to optical fiber 42 by various methods known in the art. These methods include for example, gluing, or fusing with a torch or carbon dioxide laser. In one embodiment (shown in FIG. 19), waveguide 44, optical fiber 42 and, optionally, a gradient index lens (GRIN) 46 are in communication and are held in position by heat shrinking a polymeric jacket material 49, such as polyethylene terephthalate (PET) about the optical apparatus.

FIG. 18 is a schematic illustration of another embodiment of a radiant energy emitter 40B according to the invention in which optical fiber 42 is coupled to a light diffuser 41 having light scattering particles 47 to produce a sidewise cylindrical exposure pattern of ablative radiation. This embodiment can be useful, for example, in creating a lesion within a pulmonary vein. With reference again to FIG. 1, it should be clear that the radiant energy emitter of the design shown in FIG. 14 can be advanced to the front of the projection balloon to permit diffuse exposure of a pulmonary vein ostium if a lesion is desired in that location. For further details on the construction of light diffusing elements, see U.S. Pat. No. 5,908,415 issued to Sinofsky on Jun. 1, 1999, herein incorporated by reference.

Figure 19:
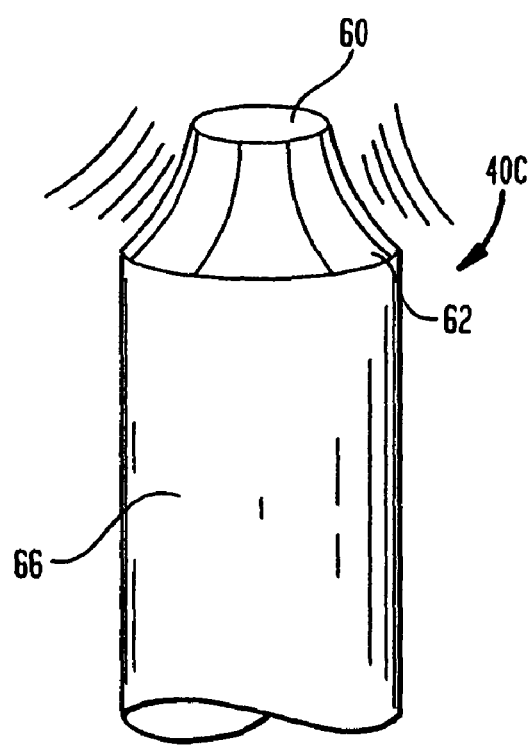
FIG. 19 is a schematic illustration of an alternative embodiment of a radiant energy emitter according to the invention employing ultrasound energy.

FIG. 19 illustrates an alternative embodiment of a radiant energy emitter 40C in which an ultrasound transducer 60 comprises individual shaped transducer elements or lenses 62, which direct the ultrasound energy into a cone of energy that can likewise form an annular exposure pattern upon impingement with a target surface. The emitter 40C is supported by a sheath 66 or similar elongate body, enclosing electrical leads, and thereby permitting the clinician to advance the emitter through an inner lumen of the instrument to a desired position for ultrasound emission.

Figure 20:
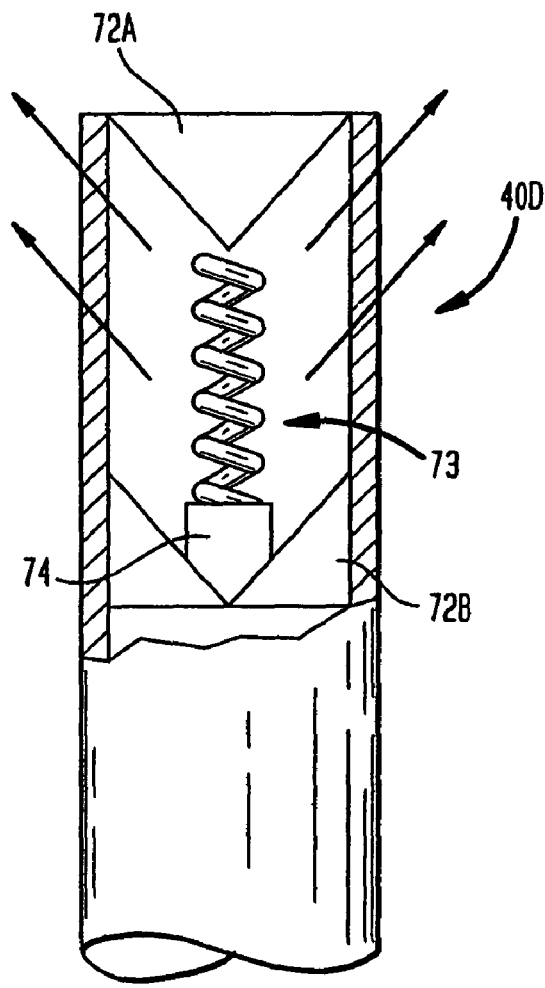
FIG. 20 is a schematic illustration of an alternative embodiment of a radiant light energy emitter according to the invention employing microwave or ionizing radiation.

Yet another embodiment of a radiant energy emitter 40D is illustrated in FIG. 20 where microwave energy is similarly focused into an annular exposure beam. As shown in FIG. 20, the radiant energy emitter can include a coaxial transmission line 74 (or similar electrical signal leads) and a helical coil antenna 73. Radiation reflectors 72A and 72B cooperate to shield and direct the radiation into a cone. In other embodiments, a radioisotope or other source of ionizing radiation can be used in lieu of the microwave antenna 73, again with appropriate radiation shielding elements 72A and 72B to project a beam of ionizing radiation.

Figure 21:
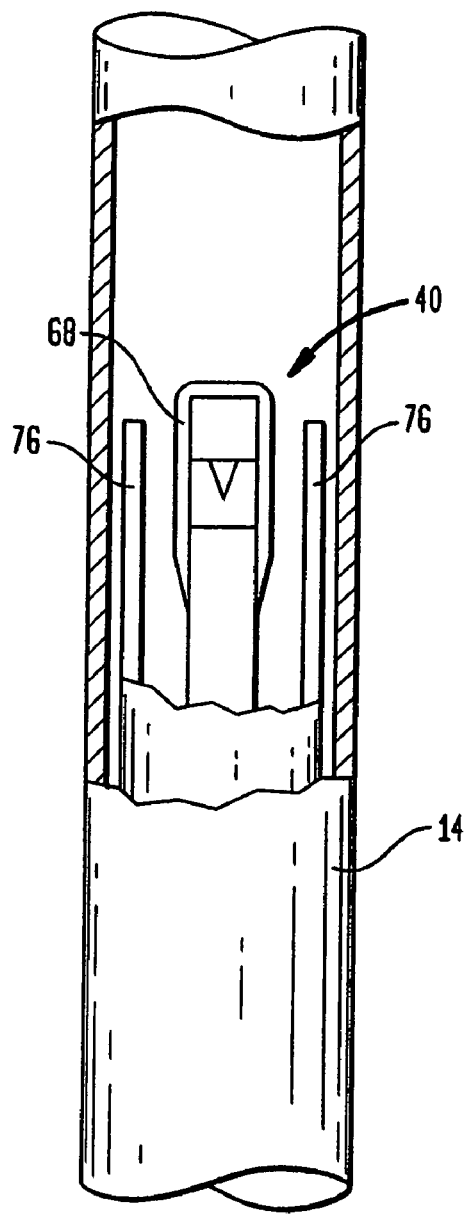
FIG. 21 is a schematic cross-sectional illustration of one embodiment of a contact sensor according to the invention.
Figure 22:
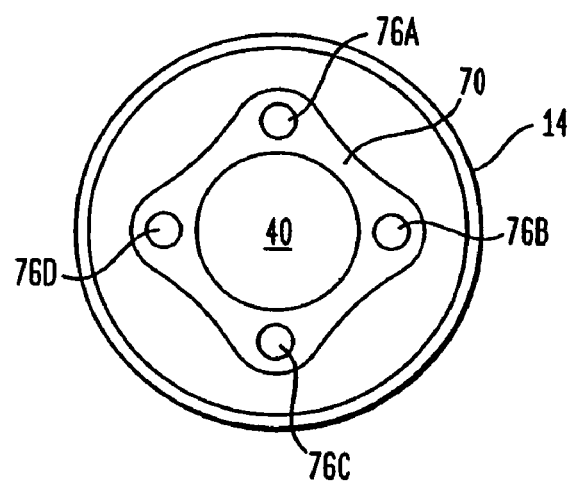
FIG. 22 is an end view, schematic illustration of the contact sensor elements shown in FIG. 21.

FIGS. 21 and 22 illustrate one embodiment of a contact sensor according to the invention incorporated into a radiant emitter assembly. The assembly can include an outer, radiant energy transparent body 70 that encases the assembly and facilitates its slidable positioning within an inner lumen of catheter body 14. The assembly further includes an energy emitter 40 (e.g., like those described above in connection with FIGS. 17-20) which can also act as the sensing fiber. In the illustrated embodiment, four illumination fibers 76A-76D are shown. If the ablative apparatus of the invention is properly positioned within the heart, light transmitted via such fibers will strike the target region, be reflected back, and be detected by the energy emitter (or other sensing element). The use of four illumination fibers allows simultaneous or sequential sensing of contact in four "quadrants." It should be clear that the invention can be practiced with various numbers of illuminating and/or sensing elements, and with or without use of the energy emitter as an element in the contact sensing module. Moreover, ultrasound emitters and detectors can also be used in the same manner in lieu of the light reflecting mechanisms to determine contact. In any event, the output signals of the sensors can be electronically processed and incorporated into a display.

The sensors of FIGS. 21-22 provide the ability to position the percutaneous ablation instruments of the present invention at a treatment site such that proper location of the energy emitter vis-à-vis the target tissue (as well a satisfactory degree of contact between the projection balloon and the tissue) is achieved. This ability is based on reflectance measurements of light scattered or absorbed by blood, body fluids, and tissue. For example, white light projected from sensing fibers 76 toward tissue has several components including red and green light. Red light has a wavelength range of about 600 to about 700 nanometers (nm) and green light has a wavelength range of about 500 to about 600 nm. When the projected light encounters blood or body fluids, most if not all green light is absorbed and hence very little green or blue light will be reflected back toward the optical assembly which includes a reflected light collector. As the apparatus is positioned such that blood and body fluids are removed from the treatment field cleared by an inflated balloon member, the reflectance of green and blue light increases as biological tissue tends to reflect more green light. As a consequence, the amount of reflected green or blue light determines whether there is blood between the apparatus and the tissue.

For example, as the instrument is positioned in a heart chamber, the green-blue reflectance signal should remain nearly at zero until the projection balloon is inflated and positioned proximal to the surface of the heart tissue. When the inflated balloon member contacts the heart tissue (or is close enough that the balloon and ablative fluid released by the instrument form a clear transmission pathway), green light is reflected back into the optical assembly and the collector. In one embodiment, only green light is projected toward the tissue surface. In another embodiment, red and green light are both projected toward the tissue surface. The red and green light can be transmitted simultaneously or separately. The use of both red and green light provides the advantage that there is no requirement that the operator needs to know how much light must be transmitted into the balloon toward the tissue surface to insure that a reflectance signal is returned. The ratio of the two different wavelengths can be measured. For example, the instrument can measure reflectance of both green light and red light. When the intensity of the light is sufficient, reflected red light is detected throughout the positioning process. Prior to contact of the instrument, and more specifically the inflated balloon, with the tissue, the ratio of red light to green light would be high. Once a transmission pathway is established, the ratio drops since more light is reflected from the tissue without any intervening blood to absorb the green light.

The reflected light is transmitted back through a collector, such as an optical fiber to a spectrophotometer. The spectrophotometer (Ocean Optics Spectrometer, Dunedin, Florida, model S-2000) produces a spectrum for each reflected pulse of reflected light. Commercially available software (LabView Software, Austin, Tex.) can isolate values for specific colors and perform ratio analyses.

In any event, the use of multiple optical fiber illumination fibers positioned about the lumen of the catheter permit the operator to determine the plane in which the catheter and balloon should be adjusted to minimize blood between the optical assembly and the treatment site. One suitable optical fiber/collector is described in U.S. Pat. No. 6,071,302, issued to Edward Sinofsky on Jun. 6, 2000, the contents of which are incorporated herein by reference.

Once the operator is satisfied with the positioning of the instrument, radiant energy can then be projected to the target tissue region. If the radiant energy is electromagnetic radiation, e.g., laser radiation, it can be emitted onto the tissue site via a separate optical fiber or, alternatively, through the same optical fiber used to transmit the white, green or red light. The laser light can be pulsed intermittently in synchronous fashion with the positioning/reflecting light to ensure that the pathway remains clear throughout the procedure.

It should be clear that the contact sensing aspects of the present invention are not limited to radiant energy ablation devices but can also be useful in placement of contact heating or cooling ablation instruments as well. For example, in FIG. 23, a contact-heating device 54 having an expandable element 56 and a contact heating element 58 is shown disposed in a pulmonary vein. The contact heating element can be a line or grid of electrically conductive material printed on the surface of the expandable element. In one embodiment, the expandable element can be substantially opaque to certain wavelengths (e.g., visible light) except for a transparent band 59, on which the contact heating element is situated. The heating wires should also be sufficiently transparent (or cover a substantially small area of the band) so as to not interfere with reflection signal collection. The device 54 can further include a sensor 76 disposed within a central lumen of the device having an illuminating fiber and a plurality of collecting fibers. The sensor 76 can be coupled to an optical detector and analyzer 53 that is located external to the device and can be used to measure light received by the sensor and determine whether contact with the target tissue has been achieved, as will be discussed in more detail below.

Figure 23:
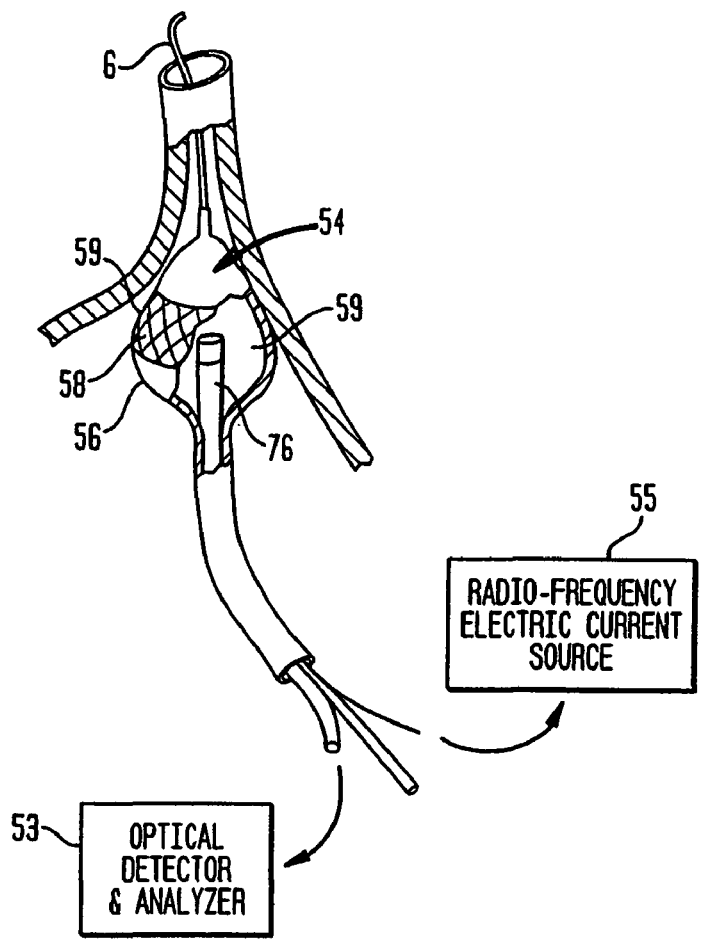
FIG. 23 is a schematic view of a contact heating ablation device employing the contacting sensing apparatus of the present invention.

The contact sensor can operate in substantially the same fashion as described above. For example, when the ablation device 54 of FIG. 23 is positioned in a pulmonary vein, and illuminated with light from within, a green-blue reflectance signal should remain nearly at zero until the expandable element 56 is inflated and positioned proximal to the surface of the heart tissue. When the portion of inflated expandable element 56 that carries the ablation band 58 contacts the heart tissue, green light is reflected back into the optical assembly and the collector. In one embodiment, only green light is projected toward the tissue surface. In another embodiment, red and green light are both projected toward the tissue surface. The red and green light can be transmitted simultaneously or separately. Again, the use of both red and green light provides the advantage that there is no requirement that the operator needs to know how much light must be transmitted into the balloon toward the tissue surface to insure that a reflectance signal is returned. The ratio of the two different wavelengths can be measured by the optical detector and analyzer 53. For example, the instrument can measure the reflectance of both green light and red light. When the intensity of the light is sufficient, reflected red light is detected throughout the positioning process. Prior to contact of the instrument, and more specifically the contact-heating ablation band, with the tissue, the ratio of red light to green light would be high. Once contact is established, the ratio drops since more light is reflected from the tissue without any intervening blood to absorb the green light, and energy can be delivered to the target tissue from, for example, a radiofrequency electric current source 55.

Figure 23A:
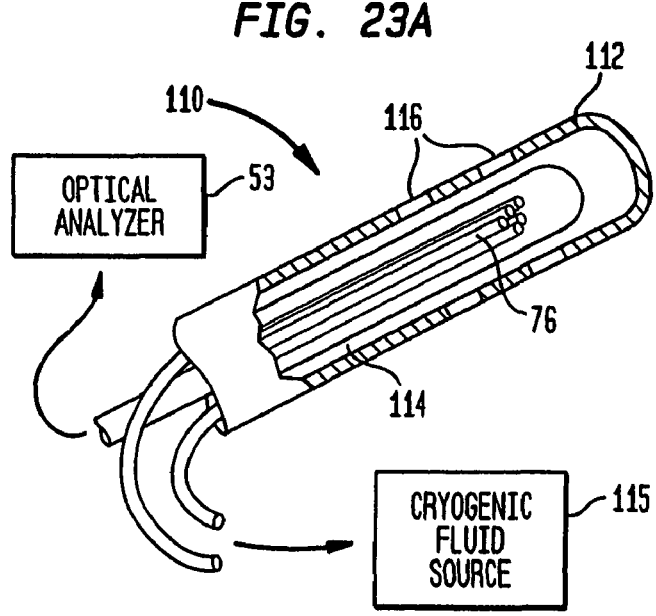
FIG. 23A is a schematic view of a cryogenic ablation device employing the contacting sensing apparatus of the present invention.

In FIG. 23A, another embodiment of a contact sensing catheter is shown in the form of a cryogenic ablation catheter 110 having a catheter body 112 and internal conduits 114 for circulation of a cryogenic fluid from a cryogenic fluid source 115. The catheter body includes conductive regions 116 where the cold temperature can be applied to tissue. The sensors 76 of the present invention can be disposed in proximity to the conductive regions, as shown and used to determine whether tissue contact has been made. For example, and similar to as discussed above with respect to FIG. 23, the sensors 76 can be coupled to an optical analyzer 53.

In FIG. 23B yet another application for the contact sensors is shown in connection with an ultrasound, contact-heating balloon catheter 120 having a balloon 122 (similar to that discussed above in connection with FIG. 23) for contacting a pulmonary vein and a band 123 for applying heat to tissue. The ultrasound ablation instrument 120 further includes transducers 124 driven by an actuator 125 to heat the ablative band 123. Again, the sensors 76 of the present invention can be disposed in proximity to the ablation band 123, as shown, and used to determine whether tissue contact has been made. For example, and similar to as discussed above with respect to FIG. 23, the sensors 76 can be coupled to an optical analyzer 53.

In FIG. 24, a translatory mechanism 80 is shown for controlled movement of a radiant energy emitter within the instruments of the present invention. The exemplary positioner 80 is incorporated into a handle 84 in the proximal region of the instrument, where the elongate body 82 of the radiant energy emitter 40 engages a thumb wheel 86 to control advancement and retraction of the emitter. It should be clear that various alternative mechanisms of manual or automated nature can be substituted for the illustrated thumb wheel 86 to position the emitter at a desired location relative to the target tissue region.

In addition, as shown in FIG. 24, the elongate body 82 that supports the radiant energy emitter 40 (e.g., an optical fiber assembly as shown in FIGS. 21-22 or the sheath for the electrical leads as shown in connection with FIGS. 19-20) can further include position indicia 92 on its surface to assist the clinician in placement of the emitter within the projection balloon. The handle can further include a window 90 whereby the user can read the indicia (e.g., gradation markers) to gauge how far the emitter has been advanced into the instrument.

Although described in connection with cardiac ablation procedures, it should be clear that the instruments of the present invention can be used for a variety of other procedures where treatment with radiant energy is desirable, including laparoscopic, endoluminal, perivisceral, endoscopic, thoracoscopic, intra-articular, and hybrid approaches.

The term "radiant energy" as used herein is intended to encompass energy sources that do not rely primarily on conductive or convective heat transfer. Such sources include, but are not limited to, acoustic and electromagnetic radiation sources and, more specifically, include microwave, x-ray, gamma-ray, and radiant light sources. The term "light" as used herein is intended to encompass electromagnetic radiation including, but not limited to, visible light, infrared, and ultraviolet radiation.

The term "continuous" in the context of a lesion is intended to mean a lesion that substantially blocks electrical conduction between tissue segments on opposite sides of the lesion. The terms "circumferential" and /or "curvilinear," including derivatives thereof, are herein intended to mean a path or line which forms an outer border or perimeter that either partially or completely surrounds a region of tissue, or separate one region of tissue from another. Further, a "circumferential" path or element may include one or more of several shapes, and may be for example, circular, annular, oblong, ovular, elliptical, or toroidal.

The term "lumen," including derivatives thereof, in the context of biological structures, is herein intended to mean any cavity or lumen within the body which is defined at least in part by a tissue wall. For example, cardiac chambers, the uterus, the regions of the gastrointestinal tract, the urinary tract, and the arterial or venous vessels are all considered illustrative examples of body spaces within the intended meaning.

The term "catheter" as used herein is intended to encompass any hollow instrument capable of penetrating body tissue or interstitial cavities and providing a conduit for selectively injecting a solution or gas, including without limitation, venous and arterial conduits of various sizes and shapes, bronchoscopes, endoscopes, cystoscopes, culpascopes, colonscopes, trocars, laparoscopes, and the like. Catheters of the present invention can be constructed with biocompatible materials known to those skilled in the art such as those listed supra, e.g., silastic, polyethylene, Teflon, polyurethanes, etc. The term "lumen," including derivatives thereof, in the context of catheters is intended to encompass any passageway within a catheter instrument (and/or track otherwise joined to such instrument that can serve as a passageway) for the passage of other component instruments or fluids or for delivery of therapeutic agents or for sampling or otherwise detecting a condition at a remote region of the instrument.

It should be understood that the term "balloon" encompasses deformable hollow shapes which can be inflated into various configurations including balloon, circular, tear drop, etc., shapes dependent upon the requirements of the body cavity. Such balloon elements can be elastic or simply capable of unfolding or unwrapping into an expanded state.

The term "transparent" is well recognized in the art and is intended to include those materials which allow transmission of energy through, for example, the primary balloon member. Preferred transparent materials do not significantly impede (e.g., result in losses of over 20 percent of energy transmitted) the energy being transferred from an energy emitter to the tissue or cell site. Suitable transparent materials include fluoropolymers, for example, fluorinated ethylene propylene (FEP), perfluoroalkoxy resin (PFA), polytetrafluoroethylene (PTFE), and ethylene-tetrafluoroethylene (ETFE).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method of treating atrial fibrillation, comprising:
   seating a distal portion of a cardiac ablation instrument against tissue at a location within a patient's heart adjacent an ostium of a pulmonary vein, the instrument having a catheter body with at least one lumen therein and an energy emitting element independently positionable along a longitudinal axis within the at least one lumen of the catheter body, wherein the instrument further includes an inflatable projection balloon that surrounds the energy emitting element and defines the distal portion that is seated at the target location, the instrument having a wave guide disposed at the distal end of the energy emitting element;
   positioning the energy emitting element at a first position relative to the catheter body moving the energy emitting element along the longitudinal axis to a first location;
   activating the energy emitting element to project ablative energy to form a first partially circumferential lesion in a proximity of the ostium of the pulmonary vein, the energy emitting element and projection balloon being constructed such that ablative energy is projected from the energy emitting element directly to a transmissive region of the projection balloon that is in contact the tissue at the target location and permits the ablative energy to pass therethrough, the ablative energy contacting the projection balloon in the transmissive region thereof;
   repositioning the energy emitting element at a second position relative to the catheter body by moving the energy emitting element along the longitudinal axis to a second location, the distal portion of the instrument remaining seated at said location;
   activating the energy emitting element to project ablative energy to form at least a second partially circumferential lesion in the proximity of the ostium of the pulmonary vein by projecting the ablative energy from the energy emitting element through the wave guide in a distal direction and at an acute angle relative to the longitudinal axis to the transmissive region of the projection balloon that permits passage of the ablative energy therethrough, the ablative energy contacting the projection balloon in the transmissive region thereof, the second partially circumferential lesion being axially combined with the first partially circumferential lesion and overlapping the first partially circumferential lesion at least one location, the distal portion of the instrument remaining seated at said location; and
   continuing the steps of repositioning the energy emitter along the longitudinal axis and activating until an axially combined lesion is formed that encircles the pulmonary vein.

2. The method of claim 1, wherein each lesion is in the shape of an arc.

3. The method of claim 1, wherein each lesion has a similar thickness.

4. The method of claim 1, further comprising adjusting the position of the energy emitting element such that the at least second lesion has a different thickness than the first lesion.

5. The method of claim 1, further comprising inflating a projection balloon to clear blood from a transmission pathway between the energy emitting element and a target region of cardiac tissue.

6. The method of claim 5, further comprising determining whether a clear transmission path exists between the energy emitting element and the target region based on reflectance measurements by an optical sensor disposed within the ablation instrument.

7. The method of claim 6, further comprising measuring at least two different wavelengths of reflected light collected by the optical sensor to determine whether a projection path has been established.

8. The method of claim 1, wherein the step of activating the energy emitting element further comprises activating a beam-forming optical waveguide to expose the target region to an annular beam of light energy to induce the combined lesion in cardiac tissue.

9. The method of claim 1, wherein the step of activating the energy emitting element further comprises activating a light emitting element to expose the target region to light energy to induce photocoagulation of cardiac tissue within the target region.

10. The method of claim 1, wherein the step of activating the energy emitting element further comprises activating a light emitting element to expose the target region to light energy to induce the combined lesion in the cardiac tissue.

11. The method of claim 1, wherein the step of activating the energy emitting element further comprises generating photoablative radiation at a wavelength in the range of about 800 nm to 1000 nm.

12. The method of claim 1, wherein the step of activating the energy emitting element further comprises generating photoablative radiation at a wavelength in the range of about 915 nm to 980 nm.

* * * * *